United States Patent
Maynard et al.

(10) Patent No.: US 6,916,827 B2
(45) Date of Patent: Jul. 12, 2005

(54) SUBSTITUTED RING-FUSED IMIDAZOLE DERIVATIVE: GABA$_A$ RECEPTORS LIGANDS

(75) Inventors: George D. Maynard, Clinton, CT (US); Jun Yuan, Guilford, CT (US); George P. Luke, Clinton, CT (US); Kevin Currie, North Branford, CT (US)

(73) Assignee: Neurogen Corporation, Branford, CT (US)

( * ) Notice: Subject to any disclaimer, the term of this patent is extended or adjusted under 35 U.S.C. 154(b) by 0 days.

(21) Appl. No.: 10/438,496

(22) Filed: May 15, 2003

(65) Prior Publication Data

US 2004/0014780 A1 Jan. 22, 2004

Related U.S. Application Data

(60) Provisional application No. 60/381,302, filed on May 17, 2002.

(51) Int. Cl.$^7$ .................. A61K 31/437; A61K 31/4184; A61K 31/506; C07D 471/04; C07D 403/06
(52) U.S. Cl. .................. 514/303; 514/256; 514/393; 514/394; 544/333; 546/118; 548/302.7; 548/306.1
(58) Field of Search .................. 546/118; 544/333; 548/302.7, 306.1; 514/303, 256, 393, 394

(56) References Cited

U.S. PATENT DOCUMENTS

| | | | |
|---|---|---|---|
| 5,130,302 A | | 7/1992 | Spielvogel et al. |
| 5,262,537 A | * | 11/1993 | Huang et al. ............... 546/118 |
| 5,362,732 A | | 11/1994 | Spielvogel et al. |
| 6,127,395 A | * | 10/2000 | DeSimone et al. ......... 514/375 |
| 6,211,365 B1 | * | 4/2001 | Albaugh et al. ............ 544/144 |
| 6,552,037 B2 | | 4/2003 | Cai et al. |
| 2003/0069257 A1 | * | 4/2003 | Li et al. ..................... 514/256 |

FOREIGN PATENT DOCUMENTS

| | | |
|---|---|---|
| EP | 0 245 637 | 11/1987 |
| EP | 0 376 624 | 7/1990 |
| EP | 0 967 220 | 4/2003 |
| WO | WO 96/39404 | 12/1996 |
| WO | WO97/26243 | 7/1997 |
| WO | WO 98/08855 | 3/1998 |
| WO | WO 02/50062 | 6/2002 |

OTHER PUBLICATIONS

Krogsgaard–Larsen P. J. Med. Chem. 1981, 24(12): 1377–1383.*
AMA Drug Evaluations (1991), Chapter 11, pp 202–210.
International Search Report for International Application PCT/US03/15578.

* cited by examiner

Primary Examiner—Evelyn Mei Huang
(74) Attorney, Agent, or Firm—McDonnell Boehnen Hulbert & Berghoff LLP

(57) ABSTRACT

Substituted ring-fused imidazole derivatives that bind to GABA$_A$ receptors are provided. Such compounds may be used to modulate ligand binding to GABA$_A$ receptors in vivo or in vitro, and are particularly useful in the treatment of a variety of central nervous system (CNS) disorders in humans, domesticated companion animals and livestock animals. Compounds provided herein may be administered alone or in combination with one or more other CNS agents to potentiate the effects of the other CNS agent(s). Pharmaceutical compositions and methods for treating such disorders are provided, as are methods for using such ligands for detecting GABA$_A$ receptors (e.g., receptor localization studies).

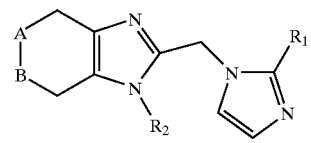

24 Claims, No Drawings

SUBSTITUTED RING-FUSED IMIDAZOLE DERIVATIVE: GABA$_A$ RECEPTORS LIGANDS

CROSS-REFERENCE TO RELATED APPLICATIONS

This application claims priority to U.S. Provisional Application 60/381,302, filed May 17, 2002.

FIELD OF THE INVENTION

This invention relates to substituted ring-fused imidazole derivatives. More specifically, it relates to ring-fused imidazolyl methyl imidazole compounds. The invention also relates to pharmaceutical compositions comprising such compounds and to the use of such compounds in the treatment of central nervous system (CNS) diseases.

BACKGROUND OF THE INVENTION

The GABA$_A$ receptor superfamily represents one of the classes of receptors through which the major inhibitory neurotransmitter, γ-aminobutyric acid, or GABA, acts. Widely, although unequally, distributed throughout the mammalian brain, GABA mediates many of its actions through a complex of proteins called the GABA$_A$ receptor, which causes alteration in chloride conductance and membrane polarization. In addition to being the site of neurotransmitter action, a number of drugs including the anxiolytic and sedating benzodiazepines bind to this receptor. The GABA$_A$ receptor comprises a chloride channel that generally, but not invariably, opens in response to GABA, allowing chloride to enter the cell. This, in turn, effects a slowing of neuronal activity through hyperpolarization of the cell membrane potential.

GABA$_A$ receptors are composed of five protein subunits. A number of cDNAs for these GABA$_A$ receptor subunits have been cloned and their primary structures determined. While these subunits share a basic motif of 4 membrane-spanning helices, there is sufficient sequence diversity to classify them into several groups. To date at least 6α, 3β, 3γ, 1ε, 1δ and 2ρ subunits have been identified. Native GABA$_A$ receptors are typically composed of 2α, 2β, and 1γ subunits (Pritchett & Seeburg *Science* 1989; 245:1389–1392, and Knight et. al., *Recept. Channels* 1998; 6:1–18). Various lines of evidence (such as message distribution, genome localization and biochemical study results) suggest that the major naturally occurring receptor combinations are $\alpha_1\beta_2\gamma_2$, $\alpha_2\beta_3\gamma_2$, $\alpha_3\beta_3\gamma_2$, and $\alpha_5\beta_3\gamma_2$ (Mohler et al. *Neuroch. Res.* 1995; 20(5):631–36).

The GABA$_A$ receptor binding sites for GABA (2 per receptor complex) are formed by amino acids from the α and β subunits. Amino acids from the α and γ subunits together form one benzodiazepine site per receptor. Benzodiazepines exert their pharmacological actions by interacting with the benzodiazepine binding sites associated with the GABA$_A$ receptor. In addition to the benzodiazepine site (sometimes referred to as the benzodiazepine or BDZ receptor), the GABA$_A$ receptor contains sites of interaction for several other classes of drugs. These include a steroid binding site, a picrotoxin site, and a barbiturate site. The benzodiazepine site of the GABA$_A$ receptor is a distinct site on the receptor complex that does not overlap with the site of interaction for other classes of drugs that bind to the receptor or for GABA (see, e.g., Cooper, et al., The Biochemical Basis of Neuropharmacology, 6$^{th}$ ed., 1991, pp. 145–148, Oxford University Press, New York).

In a classic allosteric mechanism, the binding of a drug to the benzodiazepine site increases the affinity of the GABA receptor for GABA. Benzodiazepines and related drugs that enhance the ability of GABA to open GABA$_A$ receptor channels are known as agonists or partial agonists depending on the level of GABA enhancement. Other classes of drugs, such as β-carboline derivatives, that occupy the same site and negatively modulate the action of GABA are called inverse agonists. A third class of compounds exists which occupy the same site as both the agonists and inverse agonists and yet have little or no effect on GABA activity. These compounds will, however, block the action of agonists or inverse agonists and are thus referred to as GABA$_A$ receptor antagonists.

The important allosteric modulatory effects of drugs acting at the benzodiazepine site were recognized early, and the distribution of activities at different subtype receptors has been an area of intense pharmacological discovery. Agonists that act at the benzodiazepine site are known to exhibit anxiolytic, sedative, and hypnotic effects, while compounds that act as inverse agonists at this site elicit anxiogenic, cognition enhancing, and proconvulsant effects. While benzodiazepines have enjoyed long pharmaceutical use as anxiolytics, these compounds are known to exhibit a number of unwanted side effects. These may include cognitive impairment, sedation, ataxia, potentiation of ethanol effects, and a tendency for tolerance and drug dependence.

GABA$_A$ selective ligands may also act to potentiate the effects of certain other CNS active compounds. For example, there is evidence that selective serotonin reuptake inhibitors (SSRIs) may show greater antidepressant activity when used in combination with GABA$_A$ selective ligands than when used alone.

SUMMARY OF THE INVENTION

The invention provides substituted ring-fused imidazole derivatives. The compounds of the invention bind to GABA$_A$ receptors, including human GABA$_A$ receptors and act as agonists, antagonists or inverse agonists of such receptors. These compounds are therefore useful in the treatment of a variety of CNS disorders. Preferred compounds bind with high selectivity and/or high affinity to GABA$_A$ receptors.

In a broad aspect, the invention provides compounds represented by Formula I, and pharmaceutically acceptable salts or prodrugs thereof.

Formula I

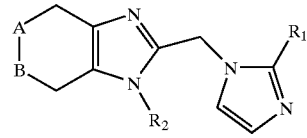

In formula I:

R$_1$ represents 5- to 10-membered aryl or heteroaryl, each of which is unsubstituted or substituted with from 1 to 4 groups independently selected from R$_5$;

R$_2$ represents C$_1$–C$_8$alkyl, C$_2$–C$_8$alkenyl, C$_2$–C$_8$alkynyl, C$_3$–C$_{10}$-cycloalkyl or (C$_3$–C$_{10}$cycloalkyl)C$_1$–C$_8$alkyl, each of which is unsubstituted or substituted with from 1 to 3 substituents independently selected from R$_5$;

either:
(a) A is CH$_2$ and B is NR$_3$ or CR$_3$R$_6$; or
(b) B is CH$_2$ and A is NR$_3$ or CR$_3$R$_6$;

$R_3$ is selected from:
(a) hydrogen, halogen, nitro and cyano; and
(b) groups of the formula:

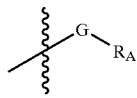

(i) G is a bond, $C_1$–$C_8$alkylene, —NH—, —N($R_B$)—, —($R_B$)N— —O—, —C(=O)—, —C(=O)NH—, —C(=O)N$R_B$—, —S(O)$_m$—, —CH$_2$C(=O)—, —S(O)$_m$NH—, —S(O)$_m$N$R_B$—, —NHC(=O)—, —C(=N$R_B$)—, HC=N—, —N$R_B$C(=O)—, —NHS(O)$_m$— or —N$R_B$S(O)—;

(ii) $R_A$ and $R_B$ are independently selected from $C_1$–$C_8$alkyl, $C_2$–$C_8$alkenyl, $C_2$–$C_8$alkynyl and 3- to 12-membered saturated, partially unsaturated and aromatic carbocycles and heterocycles having 1 ring or 2 fused, pendant and/or spiro rings, wherein each ring is unsubstituted or substituted with from 1 to 4 substituents independently selected from $R_5$; and (iii) m is 0, 1 or 2;

with the proviso that if A or B is $NR_3$, then $R_3$ is not halogen and G is not —NH—, —N($R_B$)—, —O—, —NHC(=O)—, —N$R_B$C(=O)—, —NHS(O)$_m$— or —N$R_B$S(O)—;

each $R_5$ is independently selected from halogen, hydroxy, nitro, cyano, amino, $C_1$–$C_8$alkyl, $C_1$–$C_8$alkoxy, mono- and di-($C_1$–$C_8$alkyl) amino, $C_3$–$C_{10}$cycloalkyl, ($C_3$–$C_{10}$cycloalkyl)alkyl, ($C_3$–$C_{10}$cycloalkyl) alkoxy, $C_3$–$C_9$heterocycloalkyl, $C_2$–$C_8$alkenyl, $C_2$–$C_8$alkynyl, halo($C_1$–$C_8$)alkyl, halo($C_1$–$C_8$)alkoxy, oxo, amino ($C_1$–$C_8$)alkyl and mono- and di-($C_1$–$C_8$alkyl)amino ($C_1$–$C_8$)alkyl; and $R_6$ is hydrogen or $C_1$–$C_6$alkyl.

The invention further provides pharmaceutical compositions comprising a compound as described above in combination with a physiologically acceptable carrier, solvent or excipient. Packaged pharmaceutical preparations are also provided, comprising such a pharmaceutical composition in a container and instructions for using the composition to treat a patient suffering from a CNS disorder such as anxiety, depression, a sleep disorder, attention deficit disorder or Alzheimer's dementia, or to improve short term memory.

Methods are provided, within further aspects, for the treatment of patients suffering from certain CNS disorders (such as anxiety, depression, a sleep disorder, attention deficit disorder or Alzheimer's dementia), comprising administering to a patient in need of such treatment a therapeutically effective amount of a compound as described above. The patient may be a human or other mammal. Treatment of humans, domesticated companion animals (pets) or livestock animals suffering from certain CNS disorders with an effective amount of a compound of the invention is encompassed by the invention.

Methods are also provided for enhancing short term memory in a patient, comprising administering to a patient in need of such treatment a therapeutically effective amount of a compound as described above. The patient may be a human or other mammal.

Within other aspects, the invention provides methods for potentiating a therapeutic effect of a CNS agent, comprising administering to a patient a CNS agent and a compound as described above.

Methods for determining the presence or absence of GABA$_A$ receptor in a sample (e.g., a tissue section) are further provided, comprising the steps of: (a) contacting a sample with a compound as described above under conditions that permit binding of the compound to GABA$_A$ receptor; and (b) detecting a level of compound bound to GABA$_A$ receptor.

The present invention further provides, within other aspects, methods for altering the signal-transducing activity of GABA$_A$ receptor, comprising contacting a cell expressing GABA$_A$ receptor with a compound as described above in an amount sufficient to detectably alter the electrophysiology of the cell.

These and other aspects of the invention will become apparent upon reference to the following detailed description.

DETAILED DESCRIPTION OF THE INVENTION

As noted above, the invention provides substituted ring-fused imidazole derivatives that bind (preferably with high affinity and/or high selectivity) to GABA$_A$ receptor, including human GABA$_A$ receptor. Without wishing to be bound to any particular theory, it is believed that the interaction of the compounds provided herein with the benzodiazepine site results in the biological activity of these compounds. Compounds provided herein may be used in a variety of in vivo and in vitro contexts, as discussed in further detail below.

Definitions

Compounds of the invention are generally described using standard nomenclature. Reference to a compound structure generally encompasses addition salts, hydrates and acylated prodrugs of the indicated structure. The compounds herein described may have one or more asymmetric centers or planes. Many geometric isomers of olefins, C=N double bonds, and the like can also be present in the compounds described herein, and all such stable isomers are contemplated in the present invention. Cis and trans geometric isomers of the compounds of the invention are described and may be isolated as a mixture of isomers or as separated isomeric forms. All chiral (enantiomeric and diastereomeric), and racemic forms, as well as all geometric isomeric forms of a structure are intended, unless the specific stereochemistry or isomeric form is specifically indicated.

Certain compounds are described herein using a general formula that includes variables. Unless otherwise specified, each variable within such a formula is defined independently of all other variables, and any variable that occurs more than one time within a formula is defined independently at each occurrence. Thus, for example, if a group is described as being substituted with 0–2 R*, then the group may be unsubstituted or substituted with up to two R* groups and the definition of any one R* is selected independent from the definition of any other R*. In addition, it will be apparent that combinations of substituents and/or variables are permissible only if such combinations result in stable compounds.

When any group, such as an aryl group, heteroaryl group, carbocycle or heterocycle, is said to be "substituted by one or more substituents" that group may contain from 1 to the maximum number of substituents allowable without exceeding the valency of the atoms of the substituted group. In certain embodiments, such groups are substituted with from 1 to 4 substituents or from 1 to 3 substituents. In further embodiments, such groups are unsubstituted or substituted with one oxo substituent. An "optionally substituted" group may be unsubstituted or substituted with from 1 to the maximum number of substituents indicated.

As used herein, "alkyl" refers to branched and straight-chain hydrocarbon groups. Alkyl groups include $C_1$–$C_8$alkyl (i.e., alkyl groups having from 1 to 8 carbon atoms), such as $C_1$–$C_6$alkyl and $C_1$–$C_4$alkyl. Examples of alkyl groups include, but are not limited to, methyl, ethyl, n-propyl, i-propyl, n-butyl, s-butyl, t-butyl, n-pentyl, isopentyl, s-pentyl, hexyl, 2-hexyl, 3-hexyl and 5-methylpentyl. An alkyl group may be bonded to an atom within a molecule of interest via any chemically suitable portion of the alkyl group.

The term "cycloalkyl" is intended to include saturated ring groups, having the specified number of carbon atoms, such as cyclopropyl, cyclobutyl, cyclopentyl, cyclohexyl or cycloheptyl. $C_3$–$C_{10}$cycloalkyl groups have from 3 to 10 ring members; certain cycloalkyl groups have 4 to 8 or 5 to 7 ring members.

"Heterocycloalkyl" refers to saturated ring groups that comprise at least one heteroatom (i.e., N, S or O), with the remainder of the ring members carbon. Heterocycloalkyl groups typically have from 3 to 10, from 4 to 8 or from 5 to 7 ring members. Heterocycloalkyl groups typically contain 1, 2 or 3 heteroatoms; preferably not more than one S atom and one O atom is present in a heterocycloalkyl group. Heterocycloalkyl groups include, for example, morpholinyl, piperidinyl, piperazinyl, thiomorpholinyl, and pyrrolidinyl.

In the term "(cycloalkyl)alkyl" or $(C_3$–$C_{10}$cycloalkyl) $C_1$–$C_8$alkyl, cycloalkyl and alkyl are as defined above and the point of attachment is on the alkyl group. This term encompasses, but is not limited to, cyclopropylmethyl, cyclobutylmethyl, cyclopentylmethyl, cyclohexylmethyl and cycloheptylmethyl. "(Heterocycloalkyl)alkyl" refers to such groups that comprise at least one heteroatom within the ring, as described above.

As used herein, "alkoxy" represents an alkyl group as defined above attached via an oxygen bridge. Certain alkoxy groups have from 1 to 8 carbon atoms (i.e., $C_1$–$C_8$alkoxy), 1 to 6 carbon atoms ($C_1$–$C_6$alkoxy) or 1 to 4 carbon atoms ($C_1$–$C_4$alkoxy). Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, isopentoxy, neopentoxy, n-hexoxy, 2-hexoxy, 3-hexoxy and 3-methylpentoxy.

"Alkenyl" is intended to include hydrocarbon chains of either a straight or branched configuration comprising one or more unsaturated carbon-carbon bonds which may occur in any stable point along the chain, such as ethenyl and propenyl. Alkenyl groups typically have 2 to about 8 carbon atoms, more typically 2 to about 6 carbon atoms. A "stable point" is bond that, when unsaturated, results in a chemically stable compound (i.e., a compound that can be isolated, characterized and tested for biological activity).

"Alkynyl" is intended to include hydrocarbon chains of either a straight or branched configuration comprising one or more triple carbon-carbon bonds which may occur in any stable point along the chain, such as ethynyl and propynyl. Alkynyl groups typically will have 2 to about 8 carbon atoms, more typically 2 to about 6 carbon atoms.

A "carbocycle" is a group that comprises at least one ring formed entirely by carbon-carbon bonds (referred to herein as a carbocyclic ring). Unless otherwise specified, such a ring may be aromatic or non-aromatic. A carbocycle generally has from 1 to 3 fused or pendant carbocyclic rings, preferably one ring or two fused carbocyclic rings. Typically, each ring contains from 3 to 8 (preferably from 5 to 7) ring members; carbocycles comprising fused or pendant ring systems typically contain from 9 to 12 ring members. Certain carbocycles are saturated cycloalkyl groups, as described above. Other carbocycles are "partially saturated" (i.e., comprise one or more double or triple bonds within a ring, but are not aromatic) or aryl groups (i.e., aromatic groups having 1 or more rings, wherein all members of the aromatic ring or rings are carbon). Preferred aryl groups include 5- to 10-membered groups (i.e., single 5- to 7-membered rings or 7- to 10-membered bicyclic groups), such as phenyl and naphthyl. "Arylalkyl" groups (wherein aryl and alkyl are as defined above and the point of attachment is on the alkyl group) are also encompassed by the term "carbocycle." Such groups include, but are not limited to, benzyl and phenethyl. Carbon atoms present within a carbocycle ring may, of course, be further bonded to a variety of ring substituents, such as (but not limited to) hydrogen, a halogen, hydroxy, nitro, cyano, amino, $C_1$–$C_8$alkyl, $C_1$–$C_8$alkoxy, mono- and di($C_1$–$C_8$alkyl)amino, $C_3$–$C_{10}$cycloalkyl, ($C_3$–$C_{10}$cycloalkyl)alkyl, ($C_3$–$C_{10}$cycloalkyl)alkoxy, $C_2$–$C_9$heterocycloalkyl, $C_1$–$C_8$alkenyl, $C_1$–$C_8$alkynyl, halo($C_1$–$C_8$)alkyl, halo ($C_1$–$C_8$)alkoxy, oxo, amino($C_1$–$C_8$)alkyl and mono- and di($C_1$–$C_8$alkyl)amino ($C_1$–$C_8$)alkyl.

A "heterocycle" is a group that comprises at least one ring in which at least one ring atom is a heteroatom (i.e., N, O or S), and the remainder of the ring atoms are carbon. Such a ring is referred to as a heterocyclic ring. Preferably, a heterocyclic ring comprises 1–4 heteroatoms; within certain embodiments 1 or 2 heteroatoms is preferred. A heterocycle generally has from 1 to 3 fused or pendant rings (at least one of which is heterocyclic), preferably one ring or two fused rings. Typically, each ring contains from 3 to 8 ring members (preferably from 5 to 7 ring members); heterocycles comprising fused or pendant rings typically contain from 9 to 12 ring members. 3- to 10-membered heterocyclic groups that contain 1 heterocyclic ring or 2 fused rings (at least one of which is heterocyclic; for a total of 3 to 10 ring members) are preferred, with 5- to 10-membered heterocyclic groups particularly preferred. Heterocycles may be optionally substituted with one or more substituents as described above for carbocycles. Unless otherwise specified, a heterocycle may be saturated (i.e., heterocycloalkyl, as described above), partially saturated or aromatic (heteroaryl). As used herein the term "heteroaryl" is intended to mean stable 5- to 7-membered monocyclic and 7- to 10-membered bicyclic aromatic rings, which consist of carbon atoms and from 1 to 4 ring heteroatoms independently selected from the group consisting of N, O and S. It is preferred that the total number of S and O atoms in the heteroaryl group, i.e., in the ring system, is not more than 1. In the term "heteroarylalkyl," heteroaryl and alkyl are as defined above and the point of attachment to the parent system is on the alkyl group.

Examples of heteroaryl groups include, but are not limited to, pyrimidinyl, pyridyl, quinolinyl, benzothienyl, indolyl, pryidazinyl, pyrazinyl, isoindolyl, isoquinolyl, quinazolinyl, quinoxalinyl, phthalazinyl, imidazolyl, isoxazolyl, pyrazolyl, oxazolyl, thienyl, thiazolyl, indolizinyl, indazolyl, benzothiazolyl, benzimidazolyl, benzofuranyl, benzoisoxolyl, dihydro-benzodioxinyl, furanyl, pyrrolyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinohyl, pyrrolyl N-oxide, pyrimidinyl N-oxide, pyridazinyl N-oxide, pyrazinyl N-oxide, quinolinyl N-oxide, indolyl N-oxide, indolinyl N-oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N-oxide, indazolyl N-oxide, benzothiazolyl N-oxide, benzimidazolyl N-oxide, pyrrolyl N-oxide, oxadiazolyl N-oxide, thiadiazolyl N-oxide, triazolyl N-oxide, tetrazolyl N-oxide, benzothiopyranyl S-oxide and benzothiopyranyl S,S-dioxide. Heteroaryl groups include, for example, imidazolyl, pyrrolyl, pyridyl, thiazolyl, pyrazolyl, thiazolyl, isoxazolyl, triazolyl, tetrazolyl, oxadiazolyl, pyrimidinyl and oxazolyl.

The term "halogen" includes fluorine, chlorine, bromine and iodine.

As used herein, "haloalkyl" refers to alkyl groups that are substituted with 1 or more halogen (for example —$C_vF_w$, where v is an integer of from 1 to 3 and w is an integer of from 1 to (2v+1). Examples of haloalkyl groups include, but are not limited to, mono-, di- and tri-fluoromethyl; mono-, di- and tri-chloromethyl; mono-, di-, tri-, tetra- and penta-fluoroethyl; and mono-, di-, tri-, tetra- and penta-chloroethyl. "Halo($C_1$–$C_8$)alkyl", groups have 1 to 8 carbon atoms. Preferred haloalkyl groups have 1 to 4 carbon atoms.

The term "haloalkoxy" refers to a haloalkyl group as defined above attached via an oxygen bridge. "Halo($C_1$–$C_8$) alkoxy" groups have 1 to 8 carbon atoms. Examples of haloalkoxy groups include, but are not limited to, mono-, di- and tri-fluoromethoxy. Preferred haloalkoxy groups have 1 to 4 carbon atoms.

The term "oxo," as used herein, refers to a keto (C=O) group. An oxo group that is a substituent of a nonaromatic ring results in a conversion of —$CH_2$— to —C(=O)—. It will be apparent that the introduction of an oxo substituent on an aromatic ring destroys the aromaticity.

A "substituent," as used herein, refers to a molecular moiety that is covalently bonded to an atom within a molecule of interest. For example, a "ring substituent" may be a moiety such as a halogen, alkyl group, alkoxy group, haloalkyl group or other group as discussed herein that is covalently bonded to an atom (preferably a carbon or nitrogen atom) that is a ring member. The term "substitution" refers to replacing a hydrogen atom in a molecular structure with a substituent as described above, such that the valence on the designated atom is not exceeded, and such that a chemically stable compound (i.e., a compound that can be isolated, characterized, and tested for biological activity) results from the substitution. Representative substituents include, but are not limited to, halogen, hydroxy, nitro, cyano, amino, $C_1$–$C_8$alkyl, $C_1$–$C_8$alkoxy, mono- and di($C_1$–$C_8$alkyl)amino, $C_3$–$C_{10}$cycloalkyl, ($C_3$–$C_{10}$cycloalkyl) alkyl, ($C_3$–$C_{10}$cycloalkyl) alkoxy, $C_2$–$C_9$heterocycloalkyl, $C_1$–$C_8$alkenyl, $C_1$–$C_8$alkynyl, halo ($C_1$–$C_8$)alkyl, halo($C_1$–$C_8$)alkoxy, oxo, amino($C_1$–$C_8$)alkyl and mono- and di($C_1$–$C_8$alkyl) amino ($C_1$–$C_8$)alkyl.

A dash ("—") that is not between two letters or symbols is used to indicate a point of attachment for a substituent. For example, —$CONH_2$ is attached to the parent system through the carbon atom.

The term "$GABA_A$ receptor" refers to a protein complex that detectably binds GABA and mediates a dose dependent alteration in chloride conductance and membrane polarization. Receptors comprising naturally-occurring mammalian (especially human or rat) $GABA_A$ receptor subunits are generally preferred, although subunits may be modified provided that any modifications do not substantially inhibit the receptor's ability to bind GABA (i.e., at least 50% of the binding affinity of the receptor for GABA is retained). The binding affinity of a candidate $GABA_A$ receptor for GABA may be evaluated using a standard ligand binding assay as provided herein. It will be apparent that there are a variety of $GABA_A$ receptor subtypes that fall within the scope of the term "$GABA_A$ receptor." These subtypes include, but are not limited to, $\alpha_2\beta_3\gamma_2$, $\alpha_3\beta_3\gamma_2$, $\alpha_5\beta_3\gamma_2$, and $\alpha_1\beta_2\gamma_2$ receptor subtypes. $GABA_A$ receptors may be obtained from a variety of sources, such as from preparations of rat cortex or from cells expressing cloned human $GABA_A$ receptors. Particular subtypes may be readily prepared using standard techniques (e.g., by introducing mRNA encoded the desired subunits into a host cell, as described herein).

A "prodrug" is a compound that may not fully satisfy the structural requirements of the compounds provided herein, but is modified in vivo, following administration to a patient, to produce an active compound of the present invention. For example, a prodrug may be an acylated derivative of a compound as provided herein. Prodrugs include compounds wherein hydroxy, amine or sulfhydryl groups are bonded to any group that, when administered to a mammalian subject, cleaves to form a free hydroxyl, amino or sulfhydryl group, respectively. Examples of prodrugs include, but are not limited to, acetate, formate and benzoate derivatives of alcohol and amine functional groups within the compounds provided herein.

A "patient" is any individual treated with a compound provided herein. Patients include humans, as well as other animals such as companion animals and livestock. Patients may be afflicted with a CNS disorder, or may be free of such a condition (i.e., treatment may be prophylactic).

A "CNS disorder" is a disease or condition of the central nervous system that is responsive to $GABA_A$ receptor modulation in the patient. Such disorders include anxiety disorders (e.g., panic disorder, obsessive compulsive disorder, agoraphobia, social phobia, specific phobia, dysthymia, adjustment disorders, separation anxiety, cyclothymia, and generalized anxiety disorder), stress disorders (e.g., posttraumatic stress disorder, anticipatory anxiety acute stress disorder and acute stress disorder), depressive disorders (e.g., depression, atypical depression, bipolar disorder and depressed phase of bipolar disorder), sleep disorders (e.g., primary insomnia, circadian rhythm sleep disorder, dyssomnia NOS, parasomnias including nightmare disorder, sleep terror disorder, sleep disorders secondary to depression, anxiety and/or other mental disorders and substance-induced sleep disorder), cognitive disorders (e.g., cognition impairment, mild cognitive impairment (MCI), age-related cognitive decline (ARCD), traumatic brain injury, Down's Syndrome, neurodegenerative diseases such as Alzheimer's disease and Parkinson's disease, and stroke), AIDS-associated dementia, dementia associated with depression, anxiety or psychosis, attention deficit disorders (e.g., attention deficit disorder and attention deficit and hyperactivity disorder), convulsive disorders (e.g., epilepsy), benzodiazepine overdose and drug and alcohol addiction.

A "CNS agent" is any drug used to treat or prevent a CNS disorder. CNS agents include, for example: serotonin receptor (e.g., 5-$HT_{1A}$) agonists and antagonists and selective serotonin reuptake inhibitors (SSRIs); neurokinin receptor antagonists; corticotropin releasing factor receptor ($CRF_1$) antagonists; melatonin receptor agonists; nicotinic agonists; muscarinic agents; acetylcholinesterase inhibitors and dopamine receptor agonists.

Preferred compounds of the invention bind with high selectivity and high affinity to $GABA_A$ receptors.

A compound is said to have "high affinity" if the $K_i$ at a $GABA_A$ receptor is less than 1 micromolar, preferably less than 100 nanomolar or less than 10 nanomolar. A representative assay for determining $K_i$ at $GABA_A$ receptor is provided in Example 3, herein. It will be apparent that the $K_i$ may depend upon the receptor subtype used in the assay. In other words, a high affinity compound may be "subtype-specific" (i.e., the $K_i$ is at least 10-fold greater for one subtype than for another subtype). Such compounds are said to have high affinity for $GABA_A$ receptor if the $K_i$ for at least one $GABA_A$ receptor subtype meets the above criteria.

A compound is said to have "high selectivity" if it binds to a $GABA_A$ receptor with a $K_i$ that is at least 10-fold lower, preferably at least 100-fold lower, than the $K_i$ for binding to other membrane-bound receptors. In particular, the compound should have a $K_i$ that is at least 10-fold greater at the following receptors than at a $GABA_A$ receptor: serotonin, dopamine, galanin, VR1, C5a, MCH, NPY, CRF, bradykinin, NK-1, NK-3 and tackykinin. Assays to determine the $K_i$ at other receptors may be performed using standard binding assay protocols.

Preferred compounds of Formula I are those in which $R_1$ is a 5- or 6-membered aromatic ring, unsubstituted or substituted with from 1 to 4 groups independently selected from $R_5$. Representative such $R_1$ groups include phenyl, pyridyl, pyrimidyl and thiazolyl, unsubstituted or substituted with from 1 to 3 groups independently selected from halogen, $C_1$–$C_6$alkyl, halo($C_1$–$C_6$)alkyl, $C_1$–$C_6$alkoxy and halo($C_1$–$C_6$)alkoxy. For example, $R_1$ groups may comprise one or two halogen substituents (e.g., fluorine).

$R_2$ in Formula I is, within certain embodiments, $C_1$–$C_6$alkyl or halo($C_1$–$C_6$)alkyl. For example, $R_2$ may be $C_1$–$C_4$alkyl (e.g., ethyl or propyl).

In certain embodiments, $R_3$ in Formula I is selected from hydrogen, halogen, $C_1$–$C_6$alkyl, $C_1$–$C_6$alkoxy, halo$C_1$–$C_6$alkyl, and 5- to 7-membered aromatic carbocycles and heterocycles that are unsubstituted or substituted with from 1 to 3 of halogen, nitro, cyano, trifluoromethyl or methyl. Such $R_3$ groups include, for example, $C_1$–$C_4$alkyl (such as methyl, ethyl and propyl), as well as phenyl, pyridyl or pyrimidyl, unsubstituted or substituted with from 1 to 2 of halogen, nitro, cyano, trifluoromethyl or methyl.

Certain compounds provided herein satisfy Formula II, III, IV or V, wherein variable positions are as defined above:

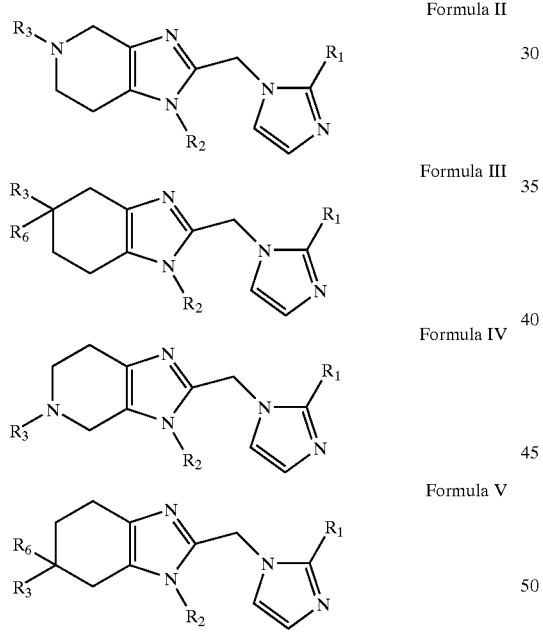

Formula II

Formula III

Formula IV

Formula V

Within certain embodiments of formulas II–V, $R_1$ is an aryl (such as phenyl or naphthyl) or 5- or 6-membered heteroaryl (e.g., pyridyl, pyrimidyl or thiazolyl), wherein each is optionally substituted with from 1 to 3 substituents independently selected from $R_5$. Preferred $R_5$ groups include halogen, $C_1$–$C_6$alkyl, halo($C_1$–$C_6$)alkyl, $C_1$–$C_6$alkoxy and halo($C_1$–$C_6$) alkoxy.

In another aspect, $R_1$ may be pyridyl, pyrimidyl or thiazolyl, each of which is optionally substituted with one or two halogens.

$R_2$, in certain embodiments of Formulas II–V, is $C_1$–$C_6$alkyl or halo($C_1$–$C_6$)alkyl. More preferably $R_2$ is $C_1$–$C_4$alkyl.

$R_3$, in certain embodiments of Formulas II–V, is hydrogen, halogen, $C_1$–$C_6$alkyl, $C_1$–$C_6$alkoxy, halo($C_1$–$C_6$) alkyl, or an aromatic carbocycle (e.g., phenyl) or 5- to 7-membered heterocycle (e.g., pyridyl or pyrimidyl), each of which is optionally substituted with from 1 to 3 substituents independently chosen from halogen, nitro, cyano, trifluoromethyl or methyl.

In certain embodiments of Formula II or IV, $R_3$ is not a halogen, or a cyano, nitro, alkoxy or amino group; $R_3$ groups in such embodiments include, for example, hydrogen and methyl.

In another aspect, the invention provides compounds of formulas II–V, wherein each $R_5$ is independently selected from halogen, hydroxy, nitro, cyano, amino, $C_1$–$C_6$alkyl, $C_1$–$C_6$alkoxy, mono- and di-($C_1$–$C_6$alkyl) amino, $C_3$–$C_7$cycloalkyl, ($C_3$–$C_7$cycloalkyl)$C_1$–$C_4$alkyl, ($C_3$–$C_7$cycloalkyl)$C_1$–$C_4$alkoxy, $C_5$–$C_6$heterocycloalkyl, $C_2$–$C_6$alkenyl, $C_2$–$C_6$alkynyl, halo($C_1$–$C_4$) alkyl, halo($C_1$–$C_4$)alkoxy, oxo, amino($C_1$–$C_6$)alkyl and mono- and di-($C_1$–$C_6$alkyl)amino($C_1$–$C_6$)alkyl; and $R_6$ is hydrogen or $C_1$–$C_6$alkyl.

In a more preferred aspect, $R_5$ and $R_6$ are as defined immediately above and $R_1$ is an aryl (such as phenyl or naphthyl) or 5- or 6-membered heteroaryl (e.g., pyridyl, pyrimidyl or thiazolyl), wherein each is optionally substituted with from 1 to 3 substituents independently selected from $R_5$.

Still more preferably, $R_5$, $R_6$, and $R_1$ are as defined immediately above and $R_2$, is $C_1$–$C_6$alkyl or halo($C_1$–$C_4$)alkyl. These compounds are hereinafter referred to as compounds of formulas IIa–Va. More preferred compounds of formulas IIa–Va are compounds wherein $R_2$ is $C_1$–$C_4$alkyl. Even more preferably, $R_2$ is ethyl.

More preferred compounds of formulas IIa–Va include compounds wherein $R_3$ is selected from:
  (a) hydrogen, halogen, nitro and cyano; and
  (b) groups of the formula:

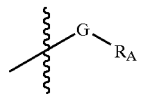

wherein:
  (i) G is a bond, or $C_1$–$C_8$alkylene;
  (ii) $R_A$ is 3- to 12-membered saturated, partially unsaturated and aromatic carbocycles and heterocycles having 1 ring or 2 fused, pendant or spiro rings, wherein each ring is unsubstituted or substituted with from 1 to 4 substituents independently selected from $R_5$;

with the proviso that if A or B is $NR_3$, then $R_3$ is not halogen and G is not —NH—, —N($R_B$)—, —O—, —NHC(=O)—, —$NR_B$C(=O)—, —NHS(O)$_m$— or —$NR_B$S(O)—.

More preferably, $R_A$ is selected from the group consisting of pyridyl, pyrimidyl, pyrazinyl, quinolinyl, imidazolyl, indolyl, phenyl, naphthyl, tetrahydronaphthyl, or $C_3$–$C_6$ cycloalkyl; wherein each is unsubstituted or substituted with from 1 to 4 $R_5$ groups. Still more preferably, $R_A$ is pyridyl, pyrimidyl, or phenyl, wherein each is unsubstituted or substituted with from 1 to 4 $R_5$ groups. Even more preferably, G is $C_1$–$C_4$ alkyl.

Other preferred compounds of formulas IIa–Va include compounds wherein
R$_3$ is selected from:
(a) hydrogen, halogen, nitro and cyano; and
(b) groups of the formula:

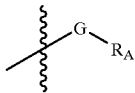

wherein:
(i) G is a bond, —NH—, —N(R$_B$)—, —(R$_B$)N— —O—, —C(=O)—, —C(=O)NH—, —C(=O)NR$_B$—, —S(O)$_m$—, —CH$_2$C(=O)—, —S(O)$_m$NH—, —S(O)$_m$NR$_B$—, —NHC(=O)—, —C(=NR$_B$)—, HC=N—, —NR$_B$C(=O)—, —NHS(O)$_m$— or —NR$_B$S(O)—;
(ii) R$_A$ and R$_B$ are independently selected from C$_1$–C$_8$alkyl, C$_2$–C$_8$alkenyl, C$_2$–C$_8$alkynyl and 3- to 12-membered saturated, partially unsaturated and aromatic carbocycles and heterocycles having 1 ring or 2 fused, pendant or spiro rings, wherein each ring is unsubstituted or substituted with from 1 to 4 substituents independently selected from R$_5$; and
(iii) m is 0, 1 or 2;
with the proviso that if A or B is NR$_3$, then R$_3$ is not halogen and G is not —NH—, —N(R$_B$)—, —O—, —NHC(=O)—, —NR$_B$C(=O)—, —NHS(O)$_m$— or —NR$_B$S(O)—.

More preferably, R$_A$ is selected from the group consisting of pyridyl, pyrimidyl, pyrazinyl, quinolinyl, imidazolyl, indolyl, phenyl, naphthyl, tetrahydronaphthyl, or C$_3$–C$_6$ cycloalkyl; wherein each is unsubstituted or substituted with from 1 to 4 R$_5$ groups. Still more preferably, R$_A$ is pyridyl, pyrimidyl, or phenyl, wherein each is unsubstituted or substituted with from 1 to 4 R$_5$ groups.

Still other preferred compounds of formulas IIa–Va include compounds wherein
R$_3$ is selected from:
(a) hydrogen, halogen, nitro and cyano; and
(b) groups of the formula:

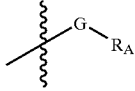

wherein:
(i) G is —NH—, —N(R$_B$)—, —(R$_B$)N— —C(=O)NR$_B$—, —CH$_2$C(=O)—, —S(O)$_m$NH—, —S(O)$_m$NR$_B$—, —NHC(=O)—, —C(=NR$_B$)—, HC=N—, —NR$_B$C(=O)—, —NHS(O)$_m$— or —NR$_B$S(O)—;
(ii) R$_A$ and R$_B$ are independently selected from C$_1$–C$_8$alkyl, C$_2$–C$_8$alkenyl, C$_2$–C$_8$alkynyl and 3- to 12-membered saturated, partially unsaturated and aromatic carbocycles and heterocycles having 1 ring or 2 fused, pendant or spiro rings, wherein each ring is unsubstituted or substituted with from 1 to 4 substituents independently selected from R$_5$; and
(iii) m is 0, 1 or 2;
with the proviso that if A or B is NR$_3$, then R$_3$ is not halogen and G is not —NH—, —N(R$_B$)—, —O—, —NHC(=O)—, —NR$_B$C(=O)—, —NHS(O)$_m$— or —NR$_B$S(O)—.

More preferably, R$_B$ is selected from C$_1$–C$_8$alkyl, C$_2$–C$_8$alkenyl, C$_2$–C$_8$alkynyl. Still more preferably, R$_A$ is then selected from the group consisting of pyridyl, pyrimidyl, pyrazinyl, quinolinyl, imidazolyl, indolyl, phenyl, naphthyl, tetrahydronaphthyl, or C$_3$–C$_6$ cycloalkyl; wherein each is unsubstituted or substituted with from 1 to 4 R$_5$ groups. Still more preferably, R$_A$ is pyridyl, pyrimidyl, or phenyl, wherein each is unsubstituted or substituted with from 1 to 4 R$_5$ groups.

Yet other preferred compounds of formulas IIa–Va include compounds wherein
R$_3$ is selected from:
(a) hydrogen, halogen, nitro and cyano; and
(b) groups of the formula:

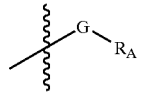

wherein:
(i) G is —O—, —C(=O)—, —S(O)$_m$—,or —CH$_2$C(=O)—;
(ii) R$_A$ is selected from C$_1$–C$_8$alkyl, C$_2$–C$_8$alkenyl, C$_2$–C$_8$alkynyl and 3- to 12-membered saturated, partially unsaturated and aromatic carbocycles and heterocycles having 1 ring or 2 fused, pendant or spiro rings, wherein each ring is unsubstituted or substituted with from 1 to 4 substituents independently selected from R$_5$; and
(iii) m is 0, 1 or 2;
with the proviso that if A or B is NR$_3$, then R$_3$ is not halogen and G is not —NH—, —N(R$_B$)—, —O—, —NHC(=O)—, —NR$_B$C(=O)—, —NHS(O)$_m$— or —NR$_B$S(O)—.

More preferably, R$_A$ is selected from the group consisting of pyridyl, pyrimidyl, pyrazinyl, quinolinyl, imidazolyl, indolyl, phenyl, naphthyl, tetrahydronaphthyl, or C$_3$–C$_6$ cycloalkyl; wherein each is unsubstituted or substituted with from 1 to 4 R$_5$ groups. Still more preferably, R$_A$ is pyridyl, pyrimidyl, or phenyl, wherein each is unsubstituted or substituted with from 1 to 4 R$_5$ groups.

In another aspect, the invention provides compounds of formula I, wherein
R$_1$ is phenyl, pyridyl or pyrimidyl, each of which is unsubstituted or substituted with from 1 to 3 groups independently selected from halogen, C$_1$–C$_6$alkyl, halo(C$_1$–C$_6$)alkyl, C$_1$–C$_6$alkoxy and halo(C$_1$–C$_6$)alkoxy;
R$_2$ is C$_1$–C$_4$alkyl;
R$_3$ is optionally substituted phenyl, pyridyl or pyrimidyl; and
R$_6$ is hydrogen.

In yet another aspect, the invention provides compounds of formula I, wherein
R$_1$ is thiazolyl;
R$_2$ is C$_1$–C$_4$alkyl;
R$_3$ is optionally substituted phenyl, pyridyl or pyrimidyl; and
R$_6$ is hydrogen.

In still yet another aspect, the invention provides compounds of formula I, wherein
R$_1$ is phenyl, pyridyl or pyrimidyl, each of which is unsubstituted or substituted with from 1 to 3 groups independently selected from halogen, C$_1$–C$_6$alkyl, halo(C$_1$–C$_6$)alkyl, C$_1$–C$_6$alkoxy and halo(C$_1$–C$_6$)alkoxy;
R$_2$ is C$_1$–C$_4$alkyl;
A or B is CR$_3$R$_6$; and
R$_3$ and R$_6$ are independently selected from hydrogen and methyl (preferably R$_6$ is hydrogen.)

Compounds provided herein detectably alter (modulate) ligand binding to GABA$_A$ receptors, as determined using a standard in vitro receptor binding assay. References herein to a "GABA_A receptor ligand binding assay" are intended to refer to the standard in vitro receptor binding assay provided in Example 3. Briefly, a competition assay may be performed in which a $GABA_A$ receptor preparation is incubated with labeled (e.g., $^3H$) ligand, such as Flumazenil, and unlabeled test compound. Incubation with a compound that detectably modulates ligand binding to $GABA_A$ receptor will result in a decrease or increase in the amount of label bound to the $GABA_A$ receptor preparation, relative to the amount of label bound in the absence of the compound. Preferably, such a compound will exhibit a $K_i$ at $GABA_A$ receptor of less than 1 micromolar, more preferably less than 500 nM, 100 nM, 20 nM or 10 nM. The $GABA_A$ receptor used to determine in vitro binding may be obtained from a variety of sources, for example from preparations of rat cortex or from cells expressing cloned human $GABA_A$ receptors.

If desired, compounds provided herein may be evaluated for certain pharmacological properties including, but not limited to, solubility, oral bioavailability, toxicity, serum protein binding, lack of clinically relevant EKG effect and in vitro and in vivo half-life. Routine assays that are well known in the art may be used to assess these properties, and identify superior compounds for a particular use. For example, solubility in aqueous solutions is preferably at least 500 ng/mL. Assays used to predict bioavailability include transport across human intestinal cell monolayers, including Caco-2 cell monolayers. Toxicity may be assessed using any standard method, such as the assay detecting an effect on cellular ATP production provided in Example 5, or toxicity to cultured hepatocytes. Penetration of the blood brain barrier of a compound in humans may be predicted from the brain levels of the compound in laboratory animals given the compound intravenously. Serum protein binding may be predicted from albumin binding assays. Such assays are described in a review by Oravcovà, et al. (Journal of Chromatography B (1996) volume 677, pages 1–27). Compound half-life is inversely proportional to the frequency of dosage of a compound. In vitro half-lives of compounds may be predicted from assays of microsomal half-life as described by Kuhnz and Gieschen (Drug Metabolism and Disposition, (1998) volume 26, pages 1120–1127).

For detection purposes, as discussed in more detail below, compounds provided herein may be isotopically-labeled or radiolabeled. Such compounds are identical to those described above, but for the fact that one or more atoms are replaced by an atom having an atomic mass or mass number different from the atomic mass or mass number usually found in nature. Examples of isotopes that can be incorporated into compounds provided herein include isotopes of hydrogen, carbon, nitrogen, oxygen, phosphorous, fluorine and chlorine, such as $^2H$, $^3H$, $^{11}C$, $^{13}C$, $^{14}C$, $^{15}N$, $^{18}O$, $^{17}O$, $^{31}P$, $^{32}P$, $^{35}S$, $^{18}F$ and $^{36}Cl$. In addition, substitution with heavy isotopes such as deuterium (i.e., $^2H$) can afford certain therapeutic advantages resulting from greater metabolic stability, for example increased in vivo half-life or reduced dosage requirements and, hence, may be preferred in some circumstances.

Preparation of Compounds

Compounds provided herein may generally be prepared using standard synthetic methods. Starting materials are generally readily available from commercial sources, such as Sigma-Aldrich Corp. (St. Louis, Mo.), or may be prepared as described herein. Representative procedures suitable for the preparation of compounds of Formula I are outlined in Schemes I and II, which are not to be construed as limiting the invention in scope or spirit to the specific reagents and conditions shown in them. Those having skill in the art will recognize that the reagents and conditions may be varied and additional steps employed to produce compounds encompassed by the invention. In some cases, protection of reactive functionalities may be necessary to achieve the desired transformations. In general, such need for protecting groups, as well as the conditions necessary to attach and remove such groups, will be apparent to those skilled in the art of organic synthesis. Unless otherwise stated in the schemes below, the variables are as defined in Formula I.

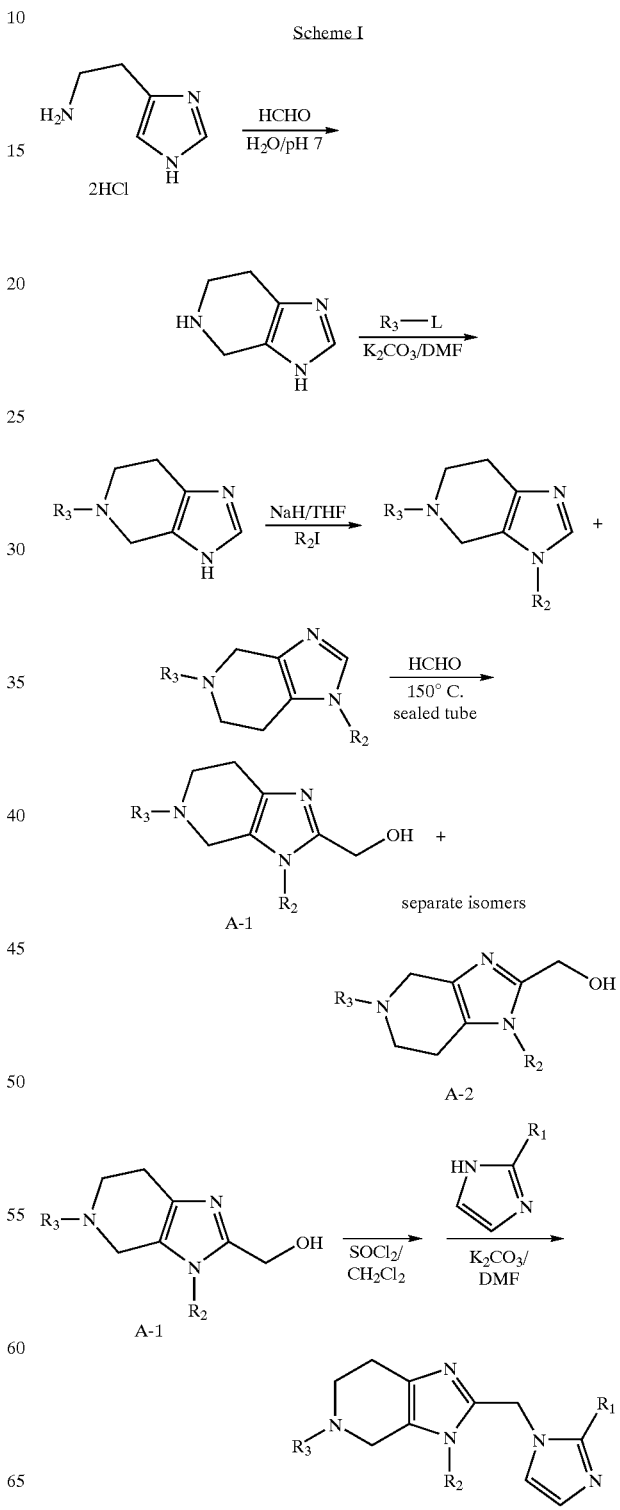

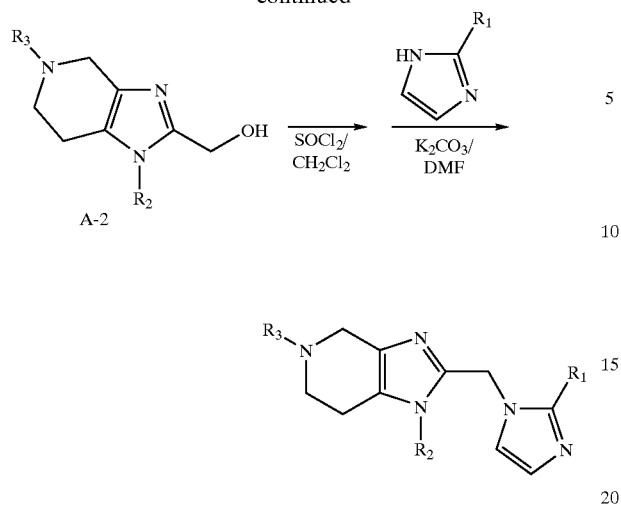

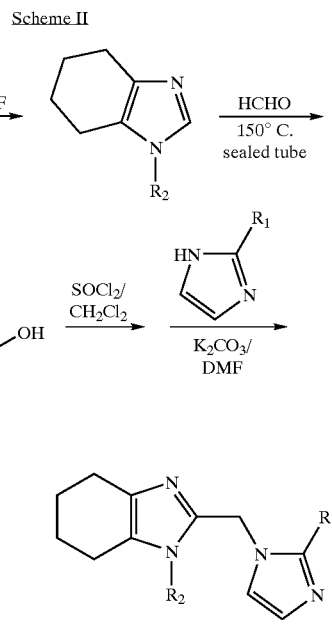

Scheme I illustrates the preparation of representative ring-fused imidazole derivatives in A or B is N. Briefly, reaction of 2-(1H-imidazol-4-yl)-ethylamine (histamine dihydrochloride; Sigma-Aldrich, St. Louis, Mo.) with formaldehyde produces 4,5,6,7-tetrahydro-1H-imidazo[4,5-c]pyridine dihydrochloride. Various $R_3$ groups may then added by reaction with the appropriate alkyl or aryl electrophile in the presence of base ($R_3$-L, wherein L is a halogen or other leaving group). Those of ordinary skill in the art will recognize that a wide variety of R3 groups may be introduced by straightforward alternate methods employing 4,5,6,7-tetrahydro-1H-imidazo[4,5-c]pyridine dihydrochloride as starting material. $R_2$ groups may be added by reaction with a suitable iodide (e.g., iodoethane). Heating in formaldehyde results in the methanol isomeric alcohols, A-1 and A-2, shown. These isomers may then be separated (e.g., via column chromatography on silica gel.) The hydroxyl group is then converted into a leaving group, such as, for example, a halide, and the leaving group is then displaced by an imidazole derivative bearing the desired $R_1$ group (prepared as shown in Scheme III.)

Scheme II illustrates the preparation of representative ring-fused imidazole derivatives wherein A is $CH_2$ and B is $CR_3R_6$, wherein $R_3$ and $R_6$ are both hydrogen. Briefly, reaction of 4,5,6,7-tetrahydro-1H-benzoimidazole (for preparation, see Chem. Ber. (1962) 95:2049, 2052–53) with a suitable iodide (e.g., iodoethane) results in the addition of $R_2$. Heating in formaldehyde results in the methanol derivative. When $R_3$ is not hydrogen, the resulting isomers may then be separated (e.g., via column chromatography on silica gel). The hydroxyl group is then converted into a leaving group, such as, for example, a halide, and the leaving group is then displaced by an imidazole derivative bearing the desired $R_1$ group (prepared as shown in Scheme III.)

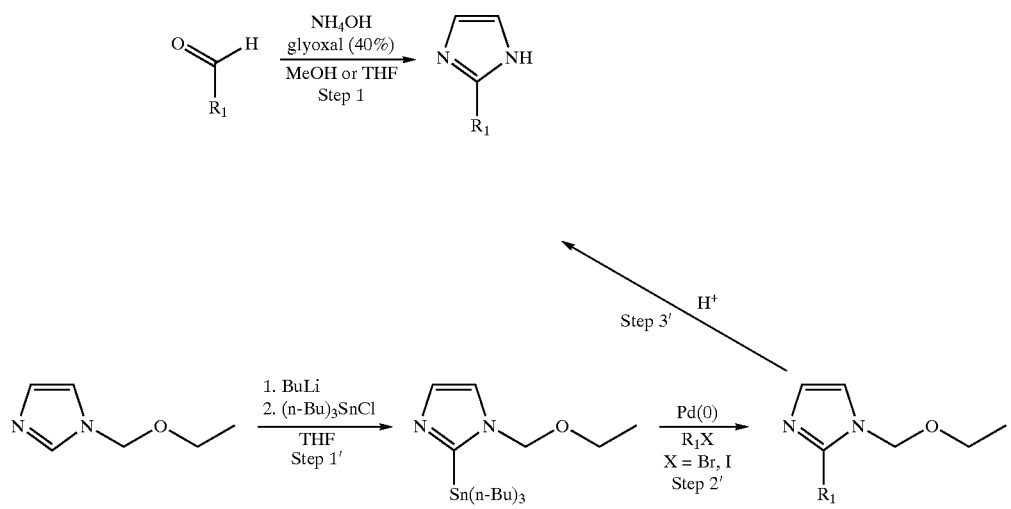

Scheme III illustrates two routes for the synthesis of $R_1$-imidazole intermediate used in Schemes I and II. In Step 1, an aryl or heteroaryl aldehyde is treated with glyoxal and ammonium hydroxide to form the $R_1$-imidazole intermediate. In Step 1', 1-ethoxymethyl-1H-imidazole is treated with butyl lithium followed by tri-n-butyltin chloride to obtain the tri-n-butylstannanyl derivative, which must be handled with care to avoid decomposition. In Step 2', the tri-n-butylstannanyl derivative is utilized in a palladium cross-coupling reaction with an aryl or heteroaryl halide to link $R_1$ to the imidazole. Subsequent treatment with acid in Step 3' provides the $R_1$-imidazole intermediate.

Scheme IV

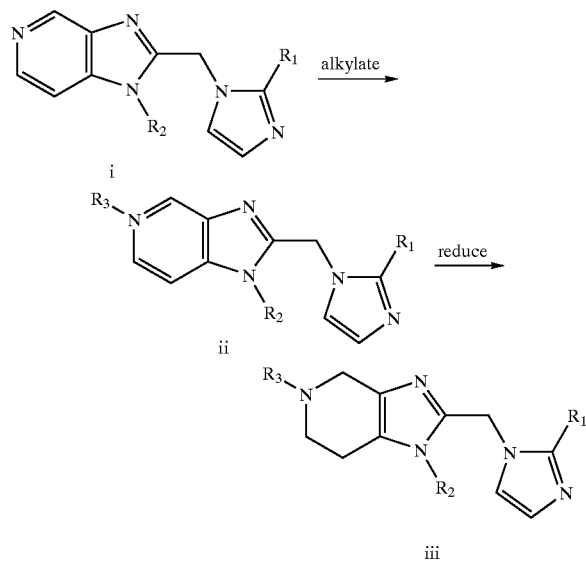

Scheme IV illustrates another method of preparing the compounds of the invention. In scheme IV, the imidazo[4,5-c]pyridine, i, is alkylated to form compound ii. Suitable alkylating agents include alkyl halides, arylalkylhalides, alkyl triflates, arylalkyltriflates, and other alkylating agents that are obvious to one of skill in the art. The alkylated material, ii, is then reduced to form the tetrahydro imidazo[4,5-c]pyridine. Suitable reducing agents include hydride reducing agents such as sodium borohydride, or LiAlH$_4$, or transition metal catalysts and hydrogen, such as PtO or Pd/C. Other useful reducing agents are known to those of skill in the art.

It will be apparent that the starting materials may be varied and additional steps employed to produce the varied compounds encompassed by the invention.

In certain situations, compounds provided herein may contain one or more asymmetric carbon atoms, so that the compounds can exist in different stereoisomeric forms. These compounds can be, for example, racemates or optically active forms. As noted above, all stereoisomers are encompassed by the invention. Nonetheless, it may be desirable to obtain single enantiomers (i.e., optically active forms). Standard methods for preparing single enantiomers include asymmetric synthesis and resolution of the racemates. Resolution of the racemates can be accomplished by conventional methods, such as crystallization in the presence of a resolving agent, or chromatography using, for example, a chiral HPLC column.

As noted above, the invention encompasses pharmaceutically acceptable salts of the compounds described herein. As used herein, a "pharmaceutically acceptable salt" is an acid or base salt that is generally considered in the art to be suitable for use in contact with the tissues of human beings or animals without excessive toxicity, irritation, allergic response, or other problem or complication, commensurate with a reasonable benefit/risk ratio. Those skilled in the art will recognize a wide variety of non-toxic pharmaceutically acceptable addition salts, including mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfinic, sulfanilic, formic, toluenesulfonic, methanesulfonic, ethane disulfonic, 2-hydroxyethylsulfonic, oxalic, isethionic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0–4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the compounds provided herein, including those listed by Remington's Pharmaceutical Sciences, 17th ed., Mack Publishing Company, Easton, Pa., p. 1418 (1985). Accordingly, the present disclosure should be construed to include all pharmaceutically acceptable salts of the compounds specifically recited.

A wide variety of synthetic procedures are available for the preparation of pharmaceutically acceptable salts. In general, a pharmaceutically acceptable salt can be synthesized from a parent compound that contains a basic or acidic moiety by any conventional chemical method. Briefly, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred.

Prodrugs of the compounds provided herein may be prepared by modifying functional groups present in the compounds in such a way that the modifications are cleaved to the parent compounds. Prodrugs include compounds wherein hydroxy, amine or sulfhydryl groups are bonded to any group that, when administered to a mammalian subject, cleaves to form a free hydroxyl, amino, or sulfhydryl group, respectively. Examples of prodrugs include, but are not limited to, acetate, formate and benzoate derivatives of alcohol and amine functional groups within the compounds provided herein. Preferred prodrugs include acylated derivatives. Those of ordinary skill in the art will recognize various synthetic methods that may be employed to prepare prodrugs of the compounds provided herein.

Compounds may be radiolabeled by carrying out their synthesis using precursors comprising at least one atom that is a radioisotope. Such radioisotope(s) are preferably selected from carbon (e.g., $^{14}C$), hydrogen (e.g., $^{3}H$), sulfur (e.g., $^{35}S$), or iodine (e.g., $^{125}I$) Synthesis of such radiolabeled compounds may be conveniently performed by a radioisotope supplier specializing in custom synthesis of radiolabeled probe compounds, such as Amersham Corporation, Arlington Heights, Ill.; Cambridge Isotope Laboratories, Inc. Andover, Mass.; SRI International, Menlo Park, Calif.; Wizard Laboratories, West Sacramento, Calif.; ChemSyn Laboratories, Lexena, Kans.; American Radiolabeled Chemicals, Inc., St. Louis, Mo.; and Moravek Biochemicals Inc., Brea, Calif. Tritium labeled compounds are also conveniently prepared catalytically via platinum-catalyzed exchange in tritiated acetic acid, acid-catalyzed exchange in tritiated trifluoroacetic acid, or heterogeneous-catalyzed exchange with tritium gas. Such preparations are also conveniently carried out as a custom radiolabeling by any of the suppliers listed above using the compound as substrate. In addition, certain precursors may be subjected to tritium-halogen exchange with tritium gas, tritium gas reduction of unsaturated bonds, or reduction using sodium borotritide, as appropriate. $^{14}$C radiolabeled compounds of the invention may be prepared using $^{14}$C radiolabeled diethyl oxalate (AMERICAN RADIOLABELED CHEMICALS, St. Louis, Mo., catalog no. ARC-1127) as a starting material for the synthesis outlined in Scheme I.

Pharmaceutical Compositions

The invention also provides pharmaceutical compositions comprising at least one compound provided herein, together with at least one physiologically acceptable carrier or excipient. Such compounds may be used for treating disorders responsive to $GABA_A$ receptor modulation (e.g., treatment of anxiety, depression, sleep disorders or cognitive impairment by $GABA_A$ receptor modulation). Pharmaceutical compositions may comprise, for example, water, buffers (e.g., neutral buffered saline or phosphate buffered saline), ethanol, mineral oil, vegetable oil, dimethylsulfoxide, carbohydrates (e.g., glucose, mannose, sucrose or dextrans), mannitol, proteins, adjuvants, polypeptides or amino acids such as glycine, antioxidants, chelating agents such as EDTA or glutathione and/or preservatives. Preferred pharmaceutical compositions are formulated for oral delivery to humans or other animals (e.g., companion animals such as dogs). If desired, other active ingredients may also be included, such as CNS agents.

Pharmaceutical compositions may be formulated for any appropriate manner of administration, including, for example, topical, oral, nasal, rectal or parenteral administration. The term parenteral as used herein includes subcutaneous, intradermal, intravascular (e.g., intravenous), intramuscular, spinal, intracranial, intrathecal and intraperitoneal injection, as well as any similar injection or infusion technique. In certain embodiments, compositions in a form suitable for oral use are preferred. Such forms include, for example, tablets, troches, lozenges, aqueous or oily suspensions, dispersible powders or granules, emulsion, hard or soft capsules, or syrups or elixirs. Within yet other embodiments, compositions of the invention may be formulated as a lyophilizate.

Compositions intended for oral use may further comprise one or more components such as sweetening agents, flavoring agents, coloring agents and preserving agents in order to provide appealing and palatable preparations. Tablets contain the active ingredient in admixture with physiologically acceptable excipients that are suitable for the manufacture of tablets. Such excipients include, for example, inert diluents (e.g., calcium carbonate, sodium carbonate, lactose, calcium phosphate or sodium phosphate), granulating and disintegrating agents (e.g., corn starch or alginic acid), binding agents (e.g., starch, gelatin or acacia) and lubricating agents (e.g., magnesium stearate, stearic acid or talc). The tablets may be uncoated or they may be coated by known techniques to delay disintegration and absorption in the gastrointestinal tract and thereby provide a sustained action over a longer period. For example, a time delay material such as glyceryl monosterate or glyceryl distearate may be employed.

Formulations for oral use may also be presented as hard gelatin capsules wherein the active ingredient is mixed with an inert solid diluent (e.g., calcium carbonate, calcium phosphate or kaolin), or as soft gelatin capsules wherein the active ingredient is mixed with water or an oil medium (e.g., peanut oil, liquid paraffin or olive oil).

Aqueous suspensions comprise the active materials in admixture with one or more excipients suitable for the manufacture of aqueous suspensions. Such excipients are suspending agents (e.g., sodium carboxymethylcellulose, methylcellulose, hydropropylmethylcellulose, sodium alginate, polyvinylpyrrolidone, gum tragacanth and gum acacia); and dispersing or wetting agents (e.g., naturally-occurring phosphatides such as lecithin, condensation products of an alkylene oxide with fatty acids such as polyoxyethylene stearate, condensation products of ethylene oxide with long chain aliphatic alcohols such as heptadecaethyleneoxycetanol, condensation products of ethylene oxide with partial esters derived from fatty acids and a hexitol such as polyoxyethylene sorbitol monooleate, or condensation products of ethylene oxide with partial esters derived from fatty acids and hexitol anhydrides such as polyethylene sorbitan monooleate). Aqueous suspensions may also contain one or more preservatives, for example ethyl, or n-propyl p-hydroxybenzoate, one or more coloring agents, one or more flavoring agents, and one or more sweetening agents, such as sucrose or saccharin.

Oily suspensions may be formulated by suspending the active ingredients in a vegetable oil (e.g., arachis oil, olive oil, sesame oil or coconut oil) or in a mineral oil such as liquid paraffin. The oily suspensions may contain a thickening agent such as beeswax, hard paraffin or cetyl alcohol. Sweetening agents such as those set forth above, and/or flavoring agents may be added to provide palatable oral preparations. Such suspension may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, such as sweetening, flavoring and coloring agents, may also be present.

Pharmaceutical compositions may also be in the form of oil-in-water emulsions. The oily phase may be a vegetable oil (e.g., olive oil or arachis oil) or a mineral oil (e.g., liquid paraffin) or mixtures thereof. Suitable emulsifying agents may be naturally-occurring gums (e.g., gum acacia or gum tragacanth), naturally-occurring phosphatides (e.g., soy bean, lecithin, and esters or partial esters derived from fatty acids and hexitol), anhydrides (e.g., sorbitan monoleate) and condensation products of partial esters derived from fatty acids and hexitol with ethylene oxide (e.g., polyoxyethylene sorbitan monooleate). The emulsions may also contain sweetening and/or flavoring agents.

Syrups and elixirs may be formulated with sweetening agents, such as glycerol, propylene glycol, sorbitol or sucrose. Such formulations may also comprise one or more demulcents, preservatives, flavoring agents and/or coloring agents.

A pharmaceutical composition may be prepared as a sterile injectible aqueous or oleaginous suspension. The compound, depending on the vehicle and concentration used, can either be suspended or dissolved in the vehicle. Such a composition may be formulated according to the known art using suitable dispersing, wetting agents and/or suspending agents such as those mentioned above. Among the acceptable vehicles and solvents that may be employed are water, 1,3-butanediol, Ringer's solution and isotonic sodium chloride solution. In addition, sterile, fixed oils may be employed as a solvent or suspending medium. For this purpose any bland fixed oil may be employed, including synthetic mono- or diglycerides. In addition, fatty acids such as oleic acid find use in the preparation of injectible compositions, and adjuvants such as local anesthetics, preservatives and/or buffering agents can be dissolved in the vehicle.

Pharmaceutical compositions may also be prepared in the form of suppositories (e.g., for rectal administration). Such compositions can be prepared by mixing the drug with a suitable non-irritating excipient that is solid at ordinary temperatures but liquid at the rectal temperature and will therefore melt in the rectum to release the drug. Suitable excipients include, for example, cocoa butter and polyethylene glycols.

For administration to non-human animals, the composition may also be added to animal feed or drinking water. It may be convenient to formulate animal feed and drinking water compositions so that the animal takes in an appropriate quantity of the composition along with its diet. It may also be convenient to present the composition as a premix for addition to feed or drinking water.

Pharmaceutical compositions may be formulated as sustained release formulations (i.e., a formulation such as a capsule that effects a slow release of compound following administration). Such formulations may generally be prepared using well known technology and administered by, for example, oral, rectal or subcutaneous implantation, or by implantation at the desired target site. Carriers for use within such formulations are biocompatible, and may also be biodegradable; preferably the formulation provides a relatively constant level of active compound release. The amount of compound contained within a sustained release formulation depends upon the site of implantation, the rate and expected duration of release and the nature of the condition to be treated or prevented.

Compounds provided herein are generally present within a pharmaceutical composition in a therapeutically effective amount. A therapeutically effective amount is an amount that results in a discernible patient benefit, such as diminution of symptoms of a CNS disorder. A preferred concentration is one sufficient to inhibit the binding of $GABA_A$ receptor ligand to $GABA_A$ receptor in vitro. Compositions providing dosage levels ranging from about 0.1 mg to about 140 mg per kilogram of body weight per day are preferred (about 0.5 mg to about 7 g per human patient per day). The amount of active ingredient that may be combined with the carrier materials to produce a single dosage form will vary depending upon the host treated and the particular mode of administration. Dosage unit forms will generally contain between from about 1 mg to about 500 mg of an active ingredient. It will be understood, however, that the optimal dose for any particular patient will depend upon a variety of factors, including the activity of the specific compound employed; the age, body weight, general health, sex and diet of the patient; the time and route of administration; the rate of excretion; any simultaneous treatment, such as a drug combination; and the type and severity of the particular disease undergoing treatment. Optimal dosages may be established using routine testing, and procedures that are well known in the art.

Pharmaceutical compositions may be packaged for treating a CNS disorder such as anxiety, depression, a sleep disorder, attention deficit disorder or Alzheimer's dementia. Packaged pharmaceutical preparations include a container holding a therapeutically effective amount of at least one compound as described herein and instructions (e.g., labeling) indicating that the contained composition is to be used for treating the CNS disorder.

Methods of Use

Within certain aspects, the invention provides methods for inhibiting the development of a CNS disorder. In other words, therapeutic methods provided herein may be used to treat a disorder, or may be used to prevent or delay the onset of such a disease in a patient who is free of detectable CNS disorder. CNS disorders are discussed in more detail below, and may be diagnosed and monitored using criteria that have been established in the art. Alternatively, or in addition, compounds provided herein may be administered to a patient to improve short-term memory. Patients include humans, domesticated companion animals (pets, such as dogs) and livestock animals, with dosages and treatment regimes as described above.

Frequency of dosage may vary, depending on the compound used and the particular disease to be treated or prevented. In general, for treatment of most disorders, a dosage regimen of 4 times daily or less is preferred. For the treatment of sleep disorders a single dose that rapidly reaches effective concentrations is desirable. Patients may generally be monitored for therapeutic effectiveness using assays suitable for the condition being treated or prevented, which will be familiar to those of ordinary skill in the art.

Within preferred embodiments, compounds provided herein are used to treat patients in need of such treatment, in an amount sufficient to alter the symptoms of a CNS disorder. Compounds that act as agonists at $\alpha_2\beta_3\gamma_2$ and $\alpha_3\beta_3\gamma_2$ receptor subtypes are particularly useful in treating anxiety disorders such as panic disorder, obsessive compulsive disorder and generalized anxiety disorder; stress disorders including post-traumatic stress, and acute stress disorders. Compounds that act as agonists at $\alpha_2\beta_3\gamma_2$ and $\alpha_3\beta_3\gamma_2$ receptor subtypes are also useful in treating depressive or bipolar disorders and in treating sleep disorders. Compounds that act as inverse agonists at the $\alpha_5\beta_3\gamma_2$ receptor subtype or $\alpha_1\beta_2\gamma_2$ and $\alpha_5\beta_3\gamma_2$ receptor subtypes are particularly useful in treating cognitive disorders including those resulting from Down's Syndrome, neurodegenerative diseases such as Alzheimer's disease and Parkinson's disease, and stroke related dementia. Compounds of the invention that act as inverse agonists at the $\alpha_5\beta_3\gamma_2$ are particularly useful in treating cognitive disorders through the enhancement of memory, and particularly short-term memory, in memory-impaired patients. Compounds that act as agonists at the $\alpha_1\beta_2\gamma_2$ receptor subtype are useful in treating convulsive disorders such as epilepsy. Compounds that act as antagonists at the benzodiazepine site are useful in reversing the effect of benzodiazepine overdose and in treating drug and alcohol addiction.

CNS disorders that can be treated using compounds and compositions provided herein include:

Depression, e.g., depression, atypical depression, bipolar disorder, depressed phase of bipolar disorder.

Anxiety, e.g., general anxiety disorder (GAD), agoraphobia, panic disorder +/− agoraphobia, social phobia, specific phobia, Post traumatic stress disorder, obsessive compulsive disorder (OCD), dysthymia, adjustment disorders with disturbance of mood and anxiety, separation anxiety disorder, anticipatory anxiety acute stress disorder, adjustment disorders, cyclothymia.

Sleep disorders, e.g., sleep disorders including primary insomnia, circadian rhythm sleep disorder, dyssomnia NOS, parasomnias, including nightmare disorder, sleep terror disorder, sleep disorders secondary to depression and/or anxiety or other mental disorders, substance induced sleep disorder.

Cognition Impairment, e.g., cognition impairment, Alzheimer's disease, Parkinson's disease, mild cognitive impairment (MCI), age-related cognitive decline (ARCD), stroke, traumatic brain injury, AIDS associated dementia, and dementia associated with depression, anxiety and psychosis (including schizophrenia and hallucinatory disorders).

Attention Deficit Disorder, e.g., attention deficit disorder (ADD), and attention deficit and hyperactivity disorder (ADHD).

Speech disorders, e.g., motor tic, clonic stuttering, dysfluency, speech blockage, dysarthria, Tourette's syndrome and logospasm.

Compounds and compositions provided herein can also be used to improve short-term memory (working memory)

in a patient. A therapeutically effective amount of a compound for improving short-term memory loss is an amount sufficient to result in a statistically significant improvement in any standard test of short-term memory function, including forward digit span and serial rote learning. For example, such a test may be designed to evaluate the ability of a patient to recall words or letters. Alternatively, a more complete neurophysical evaluation may be used to assess short-term memory function. Patients treated in order to improve short-term memory may, but need not, have been diagnosed with memory impairment or considered predisposed to development of such impairment.

In a separate aspect, the invention provides methods for potentiating the action (or therapeutic effect) of other CNS agent(s). Such methods comprise administering an effective amount of a compound provided herein in combination with another CNS agent. CNS agents include, but are not limited to the following: for anxiety, serotonin receptor (e.g., 5-$HT_{1A}$) agonists and antagonists; for anxiety and depression, neurokinin receptor antagonists or corticotropin releasing factor receptor ($CRF_1$) antagonists; for sleep disorders, melatonin receptor agonists; and for neurodegenerative disorders, such as Alzheimer's dementia, nicotinic agonists, muscarinic agents, acetylcholinesterase inhibitors and dopamine receptor agonists. Within preferred embodiments, the invention provides a method of potentiating the antidepressant activity of selective serotonin reuptake inhibitors (SSRIs) by administering an effective amount of a GABA agonist compound of the invention in combination with an SSRI. An effective amount of compound is an amount sufficient to result in a detectable change in patient symptoms, when compared to a patient treated with the other CNS agent alone.

Combination administration can be carried out in a fashion analogous to that disclosed in Da-Rocha, et al., *J. Psychopharmacology* (1997) 11(3):211–218; Smith, et al., *Am. J. Psychiatry* (1998) 155(10):1339–45; or Le, et al., *Alcohol and Alcoholism* (1996) 31(suppl.):127–132. See also PCT International Publication Nos. WO 99/47142; WO 99/47171; WO 99/47131; and WO 99/37303.

The invention also pertains to methods of inhibiting the binding of benzodiazepine compounds, such as Ro15-1788 or GABA, to the $GABA_A$ receptors. Such methods involve contacting a compound provided herein with cells expressing $GABA_A$ receptor, wherein the compound is present in an amount sufficient to inhibit benzodiazepine binding or GABA binding to $GABA_A$ receptors in vitro. This method includes inhibiting the binding of benzodiazepine compounds to $GABA_A$ receptors in vivo (e.g., in a patient given an amount of a compound provided herein that would be sufficient to inhibit the binding of benzodiazepine compounds or GABA to $GABA_A$ receptors in vitro). In one embodiment, such methods are useful in treating benzodiazepine drug overdose. The amount of a compound that would be sufficient to inhibit the binding of a benzodiazepine compound to the $GABA_A$ receptor may be readily determined via an $GABA_A$ receptor binding assay, such as the assay described in Example 3.

Within separate aspects, the invention provides a variety of in vitro uses for the compounds provided herein. For example, such compounds may be used as probes for the detection and localization of $GABA_A$ receptors, in samples such as tissue sections, as positive controls in assays for receptor activity, as standards and reagents for determining the ability of a candidate agent to bind to $GABA_A$ receptor, or as radiotracers for positron emission tomography (PET) imaging or for single photon emission computerized tomography (SPECT). Such assays can be used to characterize $GABA_A$ receptors in living subjects. Such compounds are also useful as standards and reagents in determining the ability of a potential pharmaceutical to bind to $GABA_A$ receptor.

Within methods for determining the presence or absence of $GABA_A$ receptor in a sample, a sample may be incubated with a compound as provided herein under conditions that permit binding of the compound to $GABA_A$ receptor. The amount of compound bound to $GABA_A$ receptor in the sample is then detected. For example, a compound may be labeled using any of a variety of well known techniques (e.g., radiolabeled with a radionuclide such as tritium, as described herein), and incubated with the sample (which may be, for example, a preparation of cultured cells, a tissue preparation or a fraction thereof). A suitable incubation time may generally be determined by assaying the level of binding that occurs over a period of time. Following incubation, unbound compound is removed, and bound compound detected using any method for the label employed (e.g., autoradiography or scintillation counting for radiolabeled compounds; spectroscopic methods may be used to detect luminescent groups and fluorescent groups) As a control, a matched sample may be simultaneously contacted with radiolabeled compound and a greater amount of unlabeled compound. Unbound labeled and unlabeled compound is then removed in the same fashion, and bound label is detected. A greater amount of detectable label in the test sample than in the control indicates the presence of capsaicin receptor in the sample. Detection assays, including receptor autoradiography (receptor mapping) of $GABA_A$ receptors in cultured cells or tissue samples may be performed as described by Kuhar in sections 8.1.1 to 8.1.9 of Current Protocols in Pharmacology (1998) John Wiley & Sons, New York.

For example, compounds provided herein may be used for detecting $GABA_A$ receptors in cell or tissue samples. This may be done by preparing a plurality of matched cell or tissue samples, at least one of which is prepared as an experimental sample and at least one of which is prepared as a control sample. The experimental sample is prepared by contacting (under conditions that permit binding of RO15-1788 to $GABA_A$ receptors within cell and tissue samples) at least one of the matched cell or tissue samples that has not previously been contacted with any compound provided herein with an experimental solution comprising a detectably-labeled preparation of the selected compound at the first measured molar concentration. The control sample is prepared in the same manner as the experimental sample and also contains an unlabelled preparation of the same compound at a greater molar concentration.

The experimental and control samples are then washed to remove unbound detectably-labeled compound. The amount of remaining bound detectably-labeled compound is then measured and the amount of detectably-labeled compound in the experimental and control samples is compared. A comparison that indicates the detection of a greater amount of detectable label in the at least one washed experimental sample than is detected in any of control samples demonstrates the presence of $GABA_A$ receptor in the experimental sample.

The detectably-labeled compound used in this procedure may be labeled with a radioactive label or a directly or indirectly luminescent label. When tissue sections are used in this procedure and the detectably-labeled compound is radiolabeled, the bound, labeled compound may be detected autoradiographically to generate an autoradiogram. The amount of detectable label in an experimental or control sample may be measured by viewing the autoradiograms and comparing the exposure density of the autoradiograms.

Compounds provided herein may also be used within a variety of well known cell culture and cell separation methods. For example, compounds may be linked to the interior surface of a tissue culture plate or other cell culture support, for use in immobilizing $GABA_A$ receptor-expressing cells for screens, assays and growth in culture.

Such linkage may be performed by any suitable technique, such as the methods described above, as well as other standard techniques. Compounds may also be used to facilitate cell identification and sorting in vitro, permitting the selection of cells expressing a $GABA_A$ receptor. Preferably, the compound(s) for use in such methods are labeled as described herein. Within one embodiment, a compound linked to a fluorescent marker, such as fluorescein, is contacted with the cells, which are then analyzed by fluorescence activated cell sorting (FACS).

Within other aspects, methods are provided for modulating binding of ligand to a $GABA_A$ receptor in vitro or in vivo, comprising contacting a $GABA_A$ receptor with a sufficient amount of a compound provided herein, under conditions suitable for binding of ligand to the receptor. The $GABA_A$ receptor may be present in solution, in a cultured or isolated cell preparation or within a patient. Preferably, the $GABA_A$ receptor is present in the brain of a mammal. In general, the amount of compound contacted with the receptor should be sufficient to modulate ligand binding to $GABA_A$ receptor in vitro within, for example, a binding assay as described in Example 3.

Also provided herein are methods for altering the signal-transducing activity of cellular $GABA_A$ receptor (particularly the chloride ion conductance), by contacting $GABA_A$ receptor, either in vitro or in vivo, with a sufficient amount of a compound as described above, under conditions suitable for binding of ligand to the receptor. The $GABA_A$ receptor may be present in solution, in a cultured or isolated cell preparation or within a patient, and the amount of compound may be an amount that would be sufficient to alter the signal-transducing activity of $GABA_A$ receptors in vitro. In general, the amount of compound contacted with the receptor should be sufficient to modulate ligand binding to $GABA_A$ receptor in vitro within, for example, a binding assay as described in Example 3. An effect on signal-transducing activity may be assessed as an alteration in the electrophysiology of the cells, using standard techniques. If the receptor is present in an animal, an alteration in the electrophysiology of the cell may be detected as a change in the animal's feeding behavior. The amount of a compound that would be sufficient to alter the signal-transducing activity of $GABA_A$ receptors may be determined via a $GABA_A$ receptor signal transduction assay, such as the assay described in Example 4. The cells expressing the GABA receptors in vivo may be, but are not limited to, neuronal cells or brain cells. Such cells may be contacted with compounds of the invention through contact with a body fluid containing the compound, for example through contact with cerebrospinal fluid. Alteration of the signal-transducing activity of $GABA_A$ receptors in vitro may be determined from a detectable change in the electrophysiology of cells expressing $GABA_A$ receptors, when such cells are contacted with a compound of the invention in the presence of GABA.

Intracellular recording or patch-clamp recording may be used to quantitate changes in electrophysiology of cells. A reproducible change in behavior of an animal given a compound of the invention may also be used to indicate that changes in the electrophysiology of the animal's cells expressing $GABA_A$ receptors has occurred.

The following Examples are offered by way of illustration and not by way of limitation. Unless otherwise specified all reagents and solvent are of standard commercial grade and are used without further purification. Starting materials and various intermediates may be obtained from commercial sources, prepared from commercially available organic compounds, or prepared using well known synthetic methods.

EXAMPLES

Example 1

3-Ethyl-5-(3-nitro-pyridin-2-yl)-2-(2-thiazol-2-yl-imidazol-1-ylmethyl)-4,5,6,7-tetrahydro-3H-imidazo[4,5-c]pyridine (Compound 1)

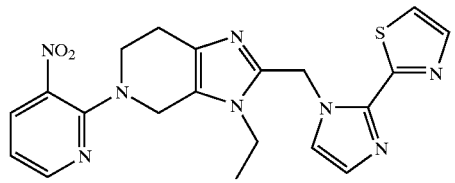

Step 1: A mixture of 4,5,6,7-tetrahydro-1H-imidazo[4,5-c]pyridine dihydrochloride (2.0 g, 12.5 mmol; prepared essentially as described by Habermehl, E., *Heterocycles* 5:127,133 (1976)), 2-chloro-3-nitropyridine (1.7 g, 11.25 mmol) and $K_2CO_3$ (5.2 g, 37.5 mmol) in 25 mL of DMF is heated at 50° C. for 4 hours and then allowed to cool to room temperature. The mixture is then partitioned between ethyl acetate and water and the layers are separated. The aqueous layer is then further extracted with ethyl acetate and the combined organic extracts are dried over $Na_2SO_4$, filtered and the solvents removed under reduced pressure. Column chromatography of the residue on silica gel (5% MeOH in $CH_2Cl_2$ as eluent) gives 5-(3-nitro-pyridin-2-yl)-4,5,6,7-tetrahydro-1H-imidazo[4,5-c]pyridine as a yellow solid (1.5 g). $^1$H NMR δ ($CDCl_3$): 8.34 (d, 1H), 8.16 (dd, 1H), 7.53(s, 1H), 6.74 (q, 1H), 4.31 (s, 2H), 3.94(t, 2H) and 2.91(t, 2H). MS: 246.3 (m+1).

Step 2: To a solution of 5-(3-nitro-pyridin-2-yl)-4,5,6,7-tetrahydro-1H-imidazo[4,5-c]pyridine (400 mg, 1.63 mmol) in 10 mL of THF is added 40% NaH in mineral oil (146 mg, 2.45 mmol). After the mixture is stirred for 20 minutes, iodoethane (760 mg, 4.89 mmol) is added. The resultant mixture is heated at 50° C. for 3 hours and allowed to cool to ambient temperature. The mixture is partitioned between ethyl acetate and water and the layers separated. The aqueous layer is further extracted with ethyl acetate and the combined organic extracts are dried over $Na_2SO_4$, filtered and the solvents removed under reduced pressure. Column chromatography of the residue on silica gel (5% MeOH in $CH_2Cl_2$ as eluent) gives a 4:1 mixture of 1-ethyl-5-(3-nitro-pyridin-2-yl)-4,5,6,7-tetrahydro-1H-imidazo[4,5-c]pyridine and 3-ethyl-5-(3-nitro-pyridin-2-yl)-4,5,6,7-tetrahydro-1H-imidazo[4,5-c]pyridine (289 mg).

Step 3: A mixture of 1-ethyl-5-(3-nitro-pyridin-2-yl)-4,5,6,7-tetrahydro-1H-imidazo[4,5-c]pyridine and 3-ethyl-5-(3-nitro-pyridin-2-yl)-4,5,6,7-tetrahydro-1H-imidazo[4,5-c]pyridine in 37% formaldehyde (5 mL) in a sealed tube is heated at 150° C. overnight. The mixture is allowed to cool to ambient temperature and evaporated under reduced pressure. The resulting residue is partitioned between ethyl acetate and water and the layers are separated. The aqueous layer is further extracted with ethyl acetate and the combined organic extracts are dried over $Na_2SO_4$, filtered and the solvents removed under reduced pressure. Column chromatography of the residue on silica gel (5% MeOH in $CH_2Cl_2$ as eluent) gives [1-ethyl-5-(3-nitro-pyridin-2-yl)-4,5,6,7-tetrahydro-1H-imidazo [4,5-c]pyridin-2-yl]-methanol (80 mg). $^1$H NMR ($CDCl_3$) δ: 8.33 (d, 1H), 8.15 (dd, 1H), 6.73 (q, 1H), 4.64 (s, 2H), 4.22 (s, 2H), 3.90–3.98 (m, 4H), 2.82(t, 2H) and 1.36 (t, 3H). MS: 304.2 (m+1).

Step 4: A solution of [1-ethyl-5-(3-nitro-pyridin-2-yl)-4,5,6,7-tetrahydro-1H-imidazo[4,5-c]pyridin-2-yl]-methanol (40 mg) in 1 M $SOCl_2$ in $CH_2Cl_2$ (5 mL) is stirred at room temperature for 1 hour and then evaporated under reduced pressure. A mixture of the resultant residue, 2-thiazol-2-yl-imidazole (20 mg; prepared as described in Example 2) and K₂CO₃ (90 mg) in 1 mL of DMF is stirred at room temperature overnight. The mixture is partitioned between ethyl acetate and water and the layers are separated. The aqueous layer is further extracted with ethyl acetate and the combined organic extracts are dried over Na₂SO₄, filtered and the solvents removed under reduced pressure. Column chromatography of the residue on silica gel (10% MeOH in CH₂Cl₂ as eluent) gives 3-Ethyl-5-(3-nitro-pyridin-2-yl)-2-(2-thiazol-2-yl-imidazol-1-ylmethyl)-4,5,6,7-tetrahydro-3H-imidazo[4,5-c]pyridine (16 mg). ¹H NMR (CDCl₃) δ: 8.33 (d, 1H), 8.18 (dd, 1H), 7.84 (d, 1H), 7.37 (d, 1H), 7.14 (s, 1H), 7.09 (s, 1H), 6.73 (q, 1H), 4.64 (s, 2H), 4.22 (s, 2H), 3.90–3.98 (m, 4H),2.82(t, 2H) and 1.36 (t, 3H).

Example 2

2-[1-Ethyl-2-(6-fluoro-pyridin-2-yl)-imidazol-1-ylmethyl)-1,4,6,7-tetrahydro-imidazo[4,5-c]pyridin-5-yl]-nicotinonitrile (Compound 2)

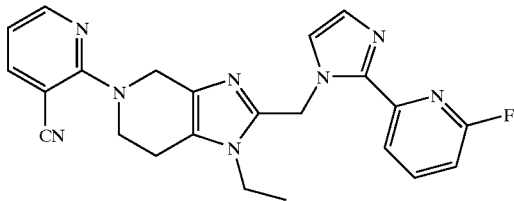

Step 1: 2-(1-ethyl-2-hydroxymethyl-3,4,6,7-tetrahydro-imidazo[4,5-c]pyridin-5-yl)-nicotinonitrile is prepared according to the procedures of Steps 1–3 above. 1H NMR (CDCl₃): 8.40 (d, 1H), 7.78 (dd, 1H), 6.70 (m, 1H), 4.60–4.70 4.64 (m, 4H), 4.00 (m, 4H), 2.85 (t, 2H) and 1.38 (t, 3H).

Step 2: A solution 2-(1-ethyl-2-hydroxymethyl-3,4,6,7-tetrahydro-imidazo[4,5-c]pyridin-5-yl)-nicotinonitrile (40 mg) in 1 M SOCl₂ in CH₂Cl₂ (5 mL) is stirred at room temperature for 1 hour and then evaporated under reduced pressure. A mixture of the resultant residue, 2-(6-fluoro-pyridin-2-yl)-imidazole (25 mg, prepared as described in Example 2) and K₂CO₃ (100 mg) in 1 mL of DMF is stirred at room temperature overnight. The mixture is partitioned between ethyl acetate and water and the layers are separated. The aqueous layer is further extracted with ethyl acetate and the combined organic extracts are dried over Na₂SO₄, filtered and the solvents removed under reduced pressure. Column chromatography of the residue on silica gel (10% MeOH in CH₂Cl₂ as eluent) gives 2-[1-ethyl-2-(6-fluoro-pyridin-2-yl)-imidazol-1-ylmethyl)-1,4,6,7-tetrahydro-imidazo[4,5-c]pyridin-5-yl]-nicotinonitrile (15 mg). 1H NMR (CDCl₃): 8.38 (d, 1H), 8.18 (dd, 1H), 7.90 (q, 1H), 7.78 (d, 1H), 7.20 (s, 1H), 7.05 (s, 1H), 6.90 (dd, 1H), 6.75 (m, 1H), 6.05 (s, 2H), 4.70 (s, 2H), 4.02 (m, 4H), 2.85 (t, 2H), 1.05 (t, 3H).

Example 3

2-[1-Ethyl-2-(2-thiazol-2-yl-imidazol-1-ylmethyl)-1,4 6,7-tetrahydro-imidazo[4,5-c]pyridin-5-yl]-nicotinonitrile (Compound 3)

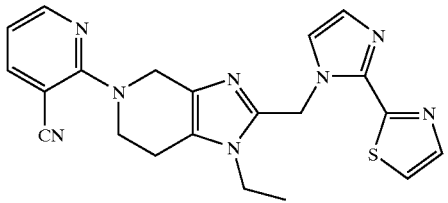

2-[1-ethyl-2-(2-thiazol-2-yl-imidazol-1-ylmethyl)-1,4,6,7-tetrahydro-imidazo[4,5-c]pyridin-5-yl]-nicotinonitrile is prepared according to the procedure of Example 1B. 1H NMR (CDCl₃): 8.31 (d, 1H), 7.85 (d, 1H), 7.78 (m, 2H), 7.38 (d, 1H), 7.16 (s, 1H), 7.09 (s, 1H), 7.70 (m, 1H), 6.70 (m, 1H), 6.10 (s, 2H), 4.71 (s, 2H), 4.03 (t, 2H), 3.90 (q, 2H), 2.84 (t, 2H), 0.96 (t, 3H).

Example 4

5-Benzyl-1-ethyl-2-(2-pyrimidin-2-yl-imidazol-1-ylmethyl)-4,5,6,7-tetrahydro-1H-imidazo[4,5-c]pyridine (Compound 4)

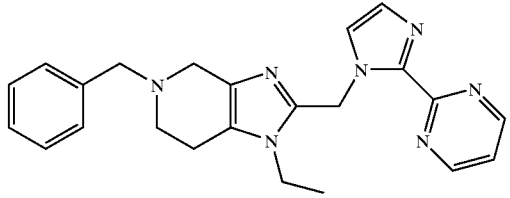

A mixture of 1-ethyl-2-(2-pyrimidin-2-yl-imidazol-1-ylmethyl)-1H-imidazo[4,5-c]pyridine (100 mg, prepared as described in Example 2) and benzyl bromide (42 mg) in 5 mL of acetone in a sealed tube is refluxed overnight and then allowed to cool. The solvent is decanted and 10 mL of MeOH is added to the residue. The resultant solution is transferred to a 25 mL flask, excess NaBH₄ is added to the solution. The reaction mixture is then stirred at room temperature for about one hour, treated with 5 mL of 1 N HCl solution and evaporated. The residue is made basic with 1N NaOH solution and extracted with CH₂Cl₂. The organic extract is dried over Na₂SO₄, filtered and the solvents removed under reduced pressure. Column chromatography of the residue on silica gel (10% MeOH in CH₂Cl₂ as eluent) gives 5-benzyl-1-ethyl-2-(2-pyrimidin-2-yl-imidazol-1-ylmethyl)-4,5,6,7-tetrahydro-1H -imidazo[4,5-c]pyridine (50 mg). 1H NMR (CDCl3): 8.85 (d, 1H), 7.20–7.40 (m, 8H), 7.10 (s, H), 6.05(s, 2H), 3.80 (q, 2H), 3.70 (s, 2H), 3,55(s, 2H), 2.78(t, 2H), 2.58 (t, 2H), 0.96 (t, 3H).

Example 5

1-Ethyl-5-methyl-2-(2-thiazol-2-yl-imidazol-1-ylmethyl)-4,5,6,7-tetrahydro-1H-imidazo[4,5-c]pyridene (Compound 5)

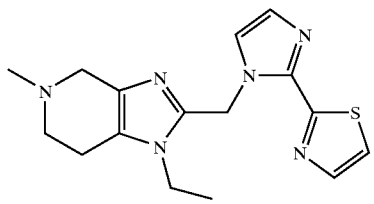

To a solution of 1-ethyl-2-(2-thiazol-2-yl-imidazol-1-ylmethyl)-1H-imidazo[4,5-c]pyridine (58 mg, 0.187 mmol, prepared as described in Example 2) in acetone is added iodomethane (0.013 mL, slightly greater than one equivalent). The resulting solution is stirred at 56° C. in a sealed tube until TLC indicates the disappearance of the starting material and the formation of a baseline spot. The acetone is then evaporated and the residue is dissolved in methanol and treated with excess $NaBH_4$. The reaction mixture is stirred at room temperature for 3 hours, and then treated with acetone to quench the excess $NaBH_4$. After the addition of 1.0 M aq NaOH, the mixture is stirred vigorously for 5 minutes and then extracted thrice with $CH_2Cl_2$. The combined extracts are dried over $K_2CO_3$ and then concentrated. The residue is purified by preparative TLC, developing with 15:1 $CHCl_3$—MeOH (+0.5% $Et_3N$). Yield: 11 mg (18%). $^1$H NMR (400 MHz, $CDCl_3$) 7.84 (d, J=3.2 Hz, 1H), 7.36 (d, J=3.2 Hz, 1H), 7.10 (s, 1H), 7.08 (s, 1H), 6.06 (s, 2H), 3.82 (q, J=7.2 Hz, 2H), 3.51 (s, 2H), 2.76 (t, J=5.6 Hz, 2H), 2.63 (t, 5.6 Hz, 2H), 2.52 (s, 3H), 0.92 (t, J=7.2 Hz, 3H) ppm. Electrospray MS: m/z 329 [M+1].

Example 6

3-Ethyl-2-[2-(3-fluoro-phenyl)-imidazol-1-ylmethyl]-5-methyl-4,5,6,7-tetrahydro-3H-imidazo[4,5-c]pyridine (Compound 6)

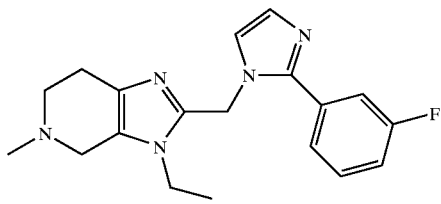

A mixture of 3-ethyl-2-[2-(3-fluoro-phenyl)-imidazol-1-ylmethyl]-3H-imidazo[4,5-c]pyridine (95 mg, 0.29 mmol; prepared as described in Example 2), methyl iodide (84 mg, 0.59 mmol) and acetone (8 mL) is heated at 60° C. for 3 hours. The mixture is cooled to room temperature and concentrated in vacuo. The residue is dissolved in ethanol (8 mL), treated portionwise with sodium borohydride (27 mg; 0.73 mmol), and stirred at room temperature for 16 hours. Water (2 mL) is added, the mixture was acidified with 2N HCl, and stirred at room temperature for 1 hour. The mixture is then made basic with 2N NaOH, extracted with dichloromethane (3×80 mL), the extracts are washed with water (1×50 mL) and brine (1×50 mL), dried over magnesium sulfate, and concentrated in vacuo to give a yellow gum. Purification by preparative thin layer chromatography over silica gel, eluting with 10% methanol in dichloromethane, gives 3-ethyl-2-[2-(3-fluoro-phenyl)-imidazol-1-ylmethyl]-5-methyl-4,5,6,7-tetrahydro-3H-imidazo[4,5-c]pyridine as a light brown oil (13 mg). LRMS calcd. 339.41, found 340.2 (MH+).

Example 7

Preparation of Representative Intermediates

This Example illustrates the synthesis of certain compounds used in the syntheses of the compounds disclosed above.

In general, intermediates may be synthesized using methods known in the art. For example, the following intermediates are synthesized as described in WO 02/50062:

| Compound | Structure | WO 02/50062 Example illustrating synthesis |
|---|---|---|
| 2-thiazol-2-yl-imidazole | 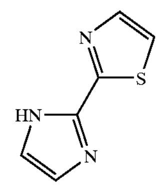 | 23 |
| 2-(6-fluoro-pyridin-2-yl)-imidazole | 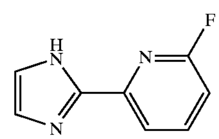 | 16 |
| 3-fluoro-(1H-imidazol-2-yl)benzene | 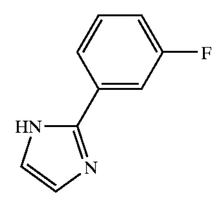 | 20 |

Other useful intermediates can be prepared as follows.

Example 8

1-Ethyl-2-(2-pyrimidin-2-yl-imidazol-1-ylmethyl)-1H-imidazo[4,5-c]pyridine

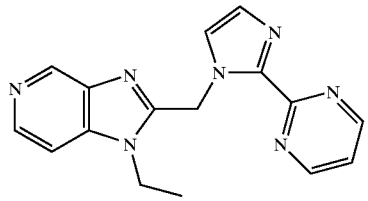

1. (2-Pyrimidin-2-yl-imidazol-1-yl)-acetic Acid Methyl Ester

To a suspension of 2-(1H-imidazol-2-yl)-pyrimidine hydrochloride (1.4 g, 7.7 mmol) in THF (50 mL) is added 40% NaH in mineral oil (675 mg, 15.4 mmol), the mixture is stirred at room temperature for one hour, and bromoacetic acid methyl ester (1.3 g, 8.4 mmol) is added. The reaction mixture is stirred at ambient temperature overnight. After aqueous $NH_4Cl$ solution (50 mL) is added, the mixture is extracted with ethyl acetate (20 mL×6) and CH$_2$Cl$_2$ (10 mL×6). The organic extracts are combined, dried over Na$_2$SO$_4$, and concentrated. The resulting residue is purified on a silica gel column with 100:10:1 CH$_2$Cl$_2$/MeOH/NH$_4$OH as eluent to yield the titled compound (650 mg).

2. Ethyl-2-(2-pyrimidin-2-yl-imidazol-1-ylmethyl)-1H-imidazo[4,5-c]pyridine

To a solution of N$^4$-ethyl-pyridine-3,4-diamine (*Justus Liebigs Ann. Chem.* (1935) 518, 274, 287) (125 mg, 0.9 mmol) in dichloroethane (10 mL) is added a solution of AlMe$_3$ in toluene (2M, 1.37 mL) dropwise under nitrogen. After addition, the mixture is stirred at room temperature for one hour and (2-pyrimidin-2-yl-imidazol-1-yl)-acetic acid methyl ester (100 mg, 0.45 mmol) is added in one portion. The reaction mixture is heated with stirring at 80° C. for 2 days. After cooled, the mixture is quenched with 5 mL of water, 2 drops of 5 N NaOH and extracted with CH$_2$Cl$_2$ (10 mL×5). The combined organic extracts are dried over Na$_2$SO$_4$, and concentrated. The residue is dissolved in 10 mL of acetic acid and the resulting mixture is heated at 100° C. overnight. After removal of acetic acid under vacuum, the residue is basified with saturated NaHCO$_3$ solution and extracted with CH$_2$Cl$_2$ (10 mL×5). The combined organic extracts are dried over Na$_2$SO$_4$, and concentrated. The residue is purified on a silica gel column with 10:1 CH$_2$Cl$_2$/MeOH as eluent to yield the title compound (40 mg). $^1$H NMR (CDCl$_3$) δ: 9.09 (s, 1H), 8.85 (d, 2H), 8.46 (d, 1H), 7.26–7.30 (m, 3H), 7.16 (1H), 6.39 (s, 2H), 4.25 (q, 2H), 1.15 (t, 3H).

Example 9

1-Ethyl-2-(2-thiazol-2-yl-imidazol-1-ylmethyl)-1H-imidazo[4,5-c]pyridine

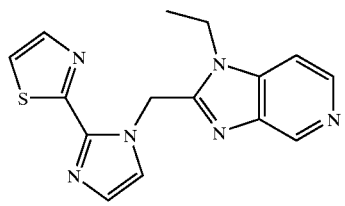

The title compound is prepared from N$^4$-ethyl-pyridine-3,4-diamine and (2-thiazol-2-yl-imidazol-1-yl)-acetic acid methyl ester following the procedure given in Example 8. $^1$H NMR (CDCl$_3$) δ 9.08 (s, 1 H), 8.43 (d, 1 H), 7.85 (d, 1 H), 7.38 (d, 1 H), 7.38–7.26 (m, 1 H), 7.17 (s, 1 H), 7.14 (s, 1 H), 6.35 (s, 2 H), 4.25 (q, 2 H), 1.11 (t, 3 H). Electrospray MS: m/z 311 [M+1]

Example 10

3-Ethyl-2-[2-(3-fluoro-phenyl)-imidazol-1-ylmethyl]-3H-imidazo[4,5-c]pyridine

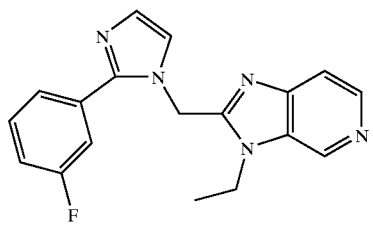

1. Preparation of 3-Chloro-4-nitro-pyridine-1-oxide

Aqueous 30% H$_2$O$_2$ (60 mL) was added dropwise to a magnetically stirred solution of 3-chloro-pyridine (12 g, 105 mmol) in acetic anhydride (60 mL) under cold conditions (0 to 10° C.). The resulting mixture is allowed to warm to room temperature slowly and stirred overnight. The reaction mixture is quenched with water (50 mL), diluted with toluene and concentrated to obtain crude N-oxide as an oil that is used without further purification.

Fuming H$_2$SO$_4$ (25 mL) is added dropwise to a solution of crude 3-chloro-pyridine-1-oxide in concentrated H$_2$SO$_4$ (25 mL) with cooling (0° C.) and stirring. HNO$_3$ (fuming, 90%, 60 mL) is added carefully to the above mixture with caution to keep the offset of any exotherm under control, and then allowed to warm up to room temperature slowly. The resulting mixture is then heated at 120° C. for 4 hours with stirring, cooled, and poured into ice-cold water, and extracted with CHCl$_3$. The combined organic phase is washed successively with saturated aqueous NaHCO$_3$, water, brine, dried over Na$_2$SO$_4$, and concentrated in vacuo to afford 3-chloro-4-nitro-pyridine-1-oxide as an yellow solid (10 g) ; $^1$H NMR (300 MHz, CDCl$_3$): $^1$H NMR (300 MHz, CDCl$_3$): δ 8.31 (d, J=1.5 Hz, 1H), 8.13 (dd, J=1.5, 5.4 Hz, 1H), 7.95 (d, J=7.2 Hz, 1H).

2. Preparation of 3-Ethylamino-4-nitro-pyridine-1-oxide

Anhydrous K$_2$CO$_3$ (19 g, 144.5 mmol) is suspended in a solution of 3-chloro-4-nitro-pyridine-1-oxide (10 g, 57.8 mmol) in anhydrous acetonitrle (100 mL). Excess diethyl amine (2.0 M) in THF is added to the above suspension with ice-bath cooling. After complete addition of ethylamine, the reaction mixture is allowed to warm to room temperature and stir overnight. The reaction mixture is filtered to remove K$_2$CO$_3$ and the filtrate is evaporated under reduced pressure to remove volatile solvents. The organic residue is subjected to chromatography eluting with 30% EtOAc-hexanes to afford 3-ethylamino-4-nitro-pyridine-1-oxide as an orange solid (8.2 g); $^1$H NMR (300 MHz, CDCl$_3$): δ 8.0 1 (d, J=7.5 Hz, 1H), 7.91(s, 1H), 7.8 (brs, NH), 7.44 (d, J=7.2 Hz, 1H), 3.30 (t, J=7.2 Hz, 2H), 1.39 (t, J=7.2 Hz, 3H), m/z 184 [M+1]

3. Preparation of N$^3$-Ethyl-pyridine-3,4-diamine

A solution of 3-ethylamino-4-nitro-pyridine 1-oxide (1.5 g, 8.19 mmol), in methanol (30 mL) is hydrogenated over 10% Pd—C (1.5 g) at 50–60 psi for 48 hours. The catalyst is removed by filtration through a pad of celite, and the solvent is evaporated under vacuum to afford N$^3$-Ethyl-pyridine-3,4-diamine as an white solid (1 g); $^1$H NMR (300 MHz, CDCl$_3$): δ 7.59 (s, 1H), 7.57 (d, J=2.4 Hz, 1H), 6.56 (d, J=5.4 Hz, 1H), 3.20 (t, J=7.2 Hz, 2H), 1.29 (t, J=7.2 Hz, 3H), m/z 138 [M+1].

The title compound, 3-ethyl-2-{[2-(3-fluorophenyl)-1H-imidazol-1-yl]methyl}-3H-imidazo[4,5-c]pyridine, is prepared from N$^3$-Ethyl-pyridine-3,4-diamine and (2-(3-fluorophenyl)-imidazol-1-yl)-acetic acid methyl ester following the procedure given in Example 2A, above. $^1$H NMR (CDCl$_3$): 8.78 (s, 1H), 8.47 (d, J=6 Hz, 1H), 7.68 (d, J=6 Hz, 1H), 7.37–7.50 (m, 3H), 7.16–7.20 (m, 2H), 7.04 (s, 1H), 5.52 (s, 2H), 3.89 (q, J=7 Hz, 2H), 1.08 (t, J=7 Hz, 3H).

Example 11

Ligand Binding Assay

The high affinity of compounds of this invention for the benzodiazepine site of the GABA$_A$ receptor was confirmed using a binding assay essentially described by Thomas and Tallman (*J. Bio. Chem.* (1981) 156:9838–9842, and *J. Neurosci.* (1983) 3:433–440).

Rat cortical tissue was dissected and homogenized in 25 volumes (w/v) of Buffer A (0.05 M Tris HCl buffer, pH 7.4 at 4° C.). The tissue homogenate was centrifuged in the cold (4° C.) at 20,000×g for 20 minutes. The supernatant was decanted, the pellet rehomogenized in the same volume of buffer, and centrifuged again at 20,000×g. The supernatant of this centrifugation step was decanted and the pellet stored at −20° C. overnight. The pellet was then thawed and resuspended in 25 volumes of Buffer A (original wt/vol), centrifuged at 20,000×g and the supernatant decanted. This wash step was repeated once. The pellet was finally resuspended in 50 volumes of Buffer A.

Incubations contained 100 µl of tissue homogenate, 100 µl of radioligand, (0.5 nM $^3$H-Ro15-1788 [$^3$H-Flumazenil], specific activity 80 Ci/mmol), and test compound or control (see below), and were brought to a total volume of 500 µl with Buffer A. Incubations were carried for 30 min at 4° C. and then rapidly filtered through Whatman GFB filters to separate free and bound ligand. Filters were washed twice with fresh Buffer A and counted in a liquid scintillation counter. Nonspecific binding (control) is determined by displacement of $^3$H Ro15-1788 with 10 µM Diazepam (Research Biochemicals International, Natick, Mass.). Data were collected in triplicate, averaged, and percent inhibition of total specific binding (Total Specific Binding=Total−Nonspecific) was calculated for each compound.

A competition binding curve was obtained with up to 11 points spanning the compound concentration range from $10^{-12}$M to $10^{-5}$M obtained per curve by the method described above for determining percent inhibition. $K_i$ values were calculated according the Cheng-Prussof equation. Each of the compounds set forth above was tested in this fashion and each was found to have a $K_i$ of <1 µM. Preferred compounds of the invention exhibit $K_i$ values of less than 100 nM and more preferred compounds of the invention exhibit $K_i$ values of less than 10 nM.

Example 12

Electrophysiology

The following assay is used to determine if a compound of the invention acts as an agonist, an antagonist, or an inverse agonist at the benzodiazepine site of the $GABA_A$ receptor.

Assays are carried out essentially as described in White and Gurley (NeuroReport 6:1313–1316, 1995) and White, Gurley, Hartnett, Stirling, and Gregory (Receptors and Channels 3:1–5, 1995) with modifications. Electrophysiological recordings are carried out using the two electrode voltage-clamp technique at a membrane holding potential of −70 mV. *Xenopus Laevis* oocytes are enzymatically isolated and injected with non-polyadenylated cRNA mixed in a ratio of 4:1:4 for α, β and γ subunits, respectively. Of the nine combinations of α, β and γ subunits described in the White et al. publications, preferred combinations are $\alpha_1\beta_2\gamma_2$, $\alpha_2\beta_3\gamma_2$, $\alpha_3\beta_3\gamma_2$, and $\alpha_5\beta_3\gamma_2$. Preferably all of the subunit cRNAs in each combination are human clones or all are rat clones. The sequence of each of these cloned subunits is available from GENBANK, e.g., human $\alpha_1$, GENBANK accession no. X14766, human $\alpha_2$, GENBANK accession no. A28100; human $\alpha_3$, GENBANK accession no. A28102; human $\alpha_5$, GENBANK accession no. A28104; human $\beta_2$, GENBANK accession no. M82919; human $\beta_3$, GENBANK accession no. Z20136; human $\gamma_2$, GENBANK accession no. X15376; rat $\alpha_1$, GENBANK accession no. L08490, rat $\alpha_2$, GENBANK accession no. L08491; rat $\alpha_3$, GENBANK accession no. L08492; rat $\alpha_5$, GENBANK accession no. L08494; rat $\beta_2$. GENBANK accession no. X15467; rat $\beta_3$. GENBANK accession no. X15468; and rat $\gamma_2$, GENBANK accession no. L08497. For each subunit combination, sufficient message for each constituent subunit is injected to provide current amplitudes of >10 nA when 1 µM GABA is applied.

Compounds are evaluated against a GABA concentration that evokes <10% of the maximal evocable GABA current (e.g., 1 µM-9 µM). Each oocyte is exposed to increasing concentrations of a compound being evaluated (test compound) in order to evaluate a concentration/effect relationship. Test compound efficacy is calculated as a percent-change in current amplitude: 100* ((Ic/I)−1), where Ic is the GABA evoked current amplitude observed in the presence of test compound and I is the GABA evoked current amplitude observed in the absence of the test compound.

Specificity of a test compound for the benzodiazepine site is determined following completion of a concentration/effect curve. After washing the oocyte sufficiently to remove previously applied test compound, the oocyte is exposed to GABA+1 µM RO15-1788, followed by exposure to GABA+1 µM RO15-1788+test compound. Percent change due to addition of compound is calculated as described above. Any percent change observed in the presence of RO15-1788 is subtracted from the percent changes in current amplitude observed in the absence of 1 µM RO15-1788. These net values are used for the calculation of average efficacy and $EC_{50}$ values by standard methods. To evaluate average efficacy and $EC_{50}$ values, the concentration/effect data are averaged across cells and fit to the logistic equation.

Example 13

MDCK Cytotoxicity Assay

This Example illustrates the evaluation of compound toxicity using a Madin Darby canine kidney (MDCK) cell cytoxicity assay.

1 µL of test compound is added to each well of a clear bottom 96-well plate (PACKARD, Meriden, Conn.) to give final concentration of compound in the assay of 10 micromolar, 100 micromolar or 200 micromolar. Solvent without test compound is added to control wells.

MDCK cells, ATCC no. CCL-34 (American Type Culture Collection, Manassas, Va.), are maintained in sterile conditions following the instructions in the ATCC production information sheet. Confluent MDCK cells are trypsinized, harvested, and diluted to a concentration of 0.1×10$^6$ cells/ml with warm (37° C.) medium (VITACELL Minimum Essential Medium Eagle, ATCC catalog # 30-2003). 100 µL of diluted cells is added to each well, except for five standard curve control wells that contain 100 µL of warm medium without cells. The plate is then incubated at 37° C. under 95% $O_2$, 5% $CO_2$ for 2 hours with constant shaking. After incubation, 50 µL of mammalian cell lysis solution is added per well, the wells are covered with PACKARD TOPSEAL stickers, and plates are shaken at approximately 700 rpm on a suitable shaker for 2 minutes.

Compounds causing toxicity will decrease ATP production, relative to untreated cells. The PACKARD, (Meriden, Conn.) ATP-LITE-M Luminescent ATP detection kit, product no. 6016941, is generally used according to the manufacturer's instructions to measure ATP production in treated and untreated MDCK cells. PACKARD ATP LITE-M reagents are allowed to equilibrate to room temperature. Once equilibrated, the lyophilized substrate solution is reconstituted in 5.5 mL of substrate buffer solution (from kit). Lyophilized ATP standard solution is reconstituted in deionized water to give a 10 mM stock. For the five control wells, 10 µL of serially diluted PACKARD standard is added to each of the standard curve control wells to yield a final concentration in each subsequent well of 200 nM, 100 nM, 50 nM, 25 nM and 12.5 nM. PACKARD substrate solution (50 µL) is added to all wells, which are then covered, and the plates are shaken at approximately 700 rpm on a suitable shaker for 2 minutes. A white PACKARD sticker is attached to the bottom of each plate and samples are dark adapted by wrapping plates in foil and placing in the dark for 10 minutes. Luminescence is then measured at 22° C. using a luminescence counter (e.g., PACKARD TOP-COUNT Microplate Scintillation and Luminescence Counter or TECAN SPECTRAFLUOR PLUS), and ATP levels calculated from the standard curve. ATP levels in cells treated with test compound(s) are compared to the levels determined for untreated cells. Cells treated with 10 μM of a preferred test compound exhibit ATP levels that are at least 80%, preferably at least 90%, of the untreated cells. When a 100 μM concentration of the test compound is used, cells treated with preferred test compounds exhibit ATP levels that are at least 50%, preferably at least 80%, of the ATP levels detected in untreated cells.

It is to be understood that the foregoing describes preferred embodiments of the invention and that modifications may be made therein without departing from the spirit or scope of the present invention.

What is claimed is:

1. A compound of the formula:

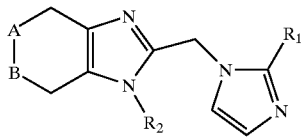

or a pharmaceutically acceptable salt thereof, wherein:
$R_1$ represents phenyl, pyridyl, thiazolyl, or pyrimidinyl, each of which is unsubstituted or substituted with from 1–3 groups independently selected from $R_5$;
$R_2$ represents $C_1$–$C_8$alkyl, $C_2$–$C_8$alkenyl, $C_2$–$C_8$alkynyl, Either:
  (a) A is $CH_2$ and B is $NR_3$ or $CR_3R_6$; or
  (b) B is $CH_2$ and A is $NR_3$ or $CR_3R_6$;
$R_3$ is independently selected from:
  (a) hydrogen, halogen, nitro and cyano; and
  (b) groups of the formula:

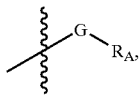

wherein: G is a bond or $C_1$–$C_6$ alkyl, and $R_A$ is hydrogen or represents phenyl, pyridyl, or pyrimidinyl, each of which is unsubstituted or substituted with from 1 to 4 substituents independently selected from $R_5$;
$R_5$ is independently selected at each occurrence from halogen, hydroxy, nitro, cyano, amino, $C_1$–$C_8$alkyl, $C_1$–$C_8$alkoxy, mono- and di($C_1$–$C_8$alkyl)amino, $C_3$–$C_{10}$cycloalkyl, ($C_3$–$C_{10}$cycloalkyl)alkyl, ($C_3$–$C_{10}$cycloalkyl)alkoxy, $C_2$–$C_9$heterocycloalkyl, $C_1$–$C_8$alkenyl, $C_1$–$C_8$alkynyl, halo($C_1$–$C_8$)alkyl, halo($C_1$–$C_8$)alkoxy, oxo, amino($C_1$–$C_8$)alkyl and mono- and di($C_1$–$C_8$alkyl)amino($C_1$–$C_8$)alkyl; and
$R_6$ is hydrogen or $C_1$–$C_6$alkyl.

2. A compound or salt according to claim 1, wherein $R_1$ is phenyl, pyridyl, pyrimidyl or thiazolyl, each of which is unsubstituted or substituted with from 1 to 3 groups independently selected from halogen, $C_1$–$C_6$alkyl, halo($C_1$–$C_6$)alkyl, $C_1$–$C_6$alkoxy and halo($C_1$–$C_6$)alkoxy.

3. A compound or salt according to claim 2, wherein $R_1$ is pyridyl, pyrimidyl or thiazolyl, each of which is unsubstituted or substituted with one or two halogens.

4. A compound or salt according to claim 1, wherein $R_2$ is $C_1$–$C_6$alkyl.

5. A compound or salt according to claim 4, wherein $R_2$ is $C_1$–$C_4$alkyl.

6. A compound or salt according to claim 1, wherein:
$R_3$ is selected from hydrogen and $C_1$–$C_6$alkyl; or
$R_3$ is phenyl, pyridyl, or pyrimidinyl each of which is unsubstituted or substituted with from 1 to 3 substituents independently chosen from halogen, nitro, cyano, trifluoromethyl and methyl.

7. A compound or salt according to claim 6, wherein $R_3$ is $C_1$–$C_4$alkyl.

8. A compound or salt according to claim 6, wherein $R_3$ is phenyl, pyridyl or pyrimidyl, each of which is unsubstituted or substituted with 1 or 2 substituents independently chosen from halogen, nitro, cyano, trifluromethyl and methyl.

9. A compound or salt according to claim 1, wherein A or B is $NR_3$.

10. A compound or salt according to claim 1, wherein A or B is $CR_3R_6$.

11. A compound or salt according to claim 1, wherein:
$R_1$ is phenyl, pyridyl or pyrimidyl, each of which is unsubstituted or substituted with from 1 to 3 groups independently selected from halogen, $C_1$–$C_6$alkyl, halo($C_1$–$C_6$)alkyl, $C_1$–$C_6$alkoxy and halo($C_1$–$C_6$)alkoxy;
$R_2$ is $C_1$–$C_4$alkyl;
$R_3$ is optionally substituted phenyl, pyridyl or pyrimidyl; and
$R_6$ is hydrogen.

12. A compound or salt according to claim 1, wherein:
$R_1$ is thiazolyl;
$R_2$ is $C_1$–$C_4$alkyl;
$R_3$ is optionally substituted phenyl, pyridyl or pyrimidyl; and
$R_6$ is hydrogen.

13. A compound or salt according to claim 1, wherein:
$R_1$ is phenyl, pyridyl or pyrimidyl, each of which is unsubstituted or substituted with from 1 to 3 groups independently selected from halogen, $C_1$–$C_6$alkyl, halo($C_1$–$C_6$)alkyl, $C_1$–$C_6$alkoxy and halo($C_1$–$C_6$)alkoxy;
$R_2$ is $C_1$–$C_4$alkyl;
A or B is $CR_3R_6$; and
$R_3$ and $R_6$ are independently selected from hydrogen and methyl.

14. A compound according to claim 1, wherein in an assay of $GABA_A$ receptor binding the compound exhibits an $K_i$ of 1 micromolar or less.

15. A compound according to claim 1, wherein in an assay of $GABA_A$ receptor binding the compound exhibits an $K_i$ of 100 nanomolar or less.

16. A compound according to claim 1, wherein in an assay of $GABA_A$ receptor binding the compound exhibits an $K_i$ of 10 nanomolar or less.

17. A compound according to claim 1, which is 3-ethyl-5-(3-nitro-pyridin-2-yl)-2-(2-thiazol-2-yl-imidazol-1-methyl)-4,5,6,7-tetrahydro-3H-imidazo[4,5-c]pyridine.

18. A compound according to claim 1, which is 2-[1-ethyl-2-(6-fluoro-pyridin-2-yl)-imidazol-1-ylmethyl)-1,4,6,7-tetrahydro-imidazo[4,5-c]pyridin-5-yl]-nicotinonitrile.

19. A compound according to claim 1, which is 2-[1-ethyl-2-(2-thiazol-2-yl-imidazol-1-ylmethyl)-1,4,6,7-tetrahydro-imidazo[4,5-c]pyridin-5-yl]-nicotinonitrile.

20. A compound according to claim 1, which is 5-benzyl-1-ethyl-2-(2-pyrimidin-2-yl-imidazol-1-ylmethyl)-4,5,6,7-tetrahydro-1H-imidazo[4,5-c]pyridine.

21. A compound according to claim 1, which is 1-ethyl-5-methyl-2-(2-thiazol-2-yl-imidazol-1-ylmethyl)-4,5,6,7-tetrahydro-1H-imidazo[4,5-c]pyridine.

22. A compound according to claim 1, which is 3-ethyl-2-[2-(3-fluoro-phenyl)-imidazol-1-ylmethyl]-5-methyl-4,5,6,7-tetrahydro-3H-imidazo-[4,5-c]pyridine.

23. A pharmaceutical composition comprising a compound according to claim 1, in combination with a physiologically acceptable carrier or excipient.

24. The pharmaceutical composition of claim 23, wherein the pharmaceutical composition is formulated as an injectible fluid, an aerosol, a cream, a gel, a pill, a capsule, a syrup, or a transdermal patch.

* * * * *